United States Patent
Kim et al.

(10) Patent No.: US 10,245,590 B2
(45) Date of Patent: Apr. 2, 2019

(54) HIGH-SPEED REAL-TIME PCR DEVICE BASED ON LAB-ON-A-CHIP FOR DETECTING FOOD-BORNE BACTERIA TO AGRIFOOD, AND METHODS FOR DETECTING FOOD-BORNE BACTERIA TO AGRIFOOD USING THE SAME

(71) Applicant: NANOBIOSYS INC., Seoul (KR)

(72) Inventors: Sung Woo Kim, Seoul (KR); Mi-Ree Kim, Asan-si (KR)

(73) Assignee: NANOBIOSYS INC., Seoul (KR)

( * ) Notice: Subject to any disclaimer, the term of this patent is extended or adjusted under 35 U.S.C. 154(b) by 219 days.

(21) Appl. No.: 15/109,078

(22) PCT Filed: Dec. 30, 2014

(86) PCT No.: PCT/KR2014/013058
§ 371 (c)(1),
(2) Date: Jun. 29, 2016

(87) PCT Pub. No.: WO2015/102379
PCT Pub. Date: Jul. 9, 2015

(65) Prior Publication Data
US 2017/0157614 A1    Jun. 8, 2017

(30) Foreign Application Priority Data
Dec. 31, 2013 (KR) ........................ 10-2013-0168689

(51) Int. Cl.
| C12P 19/34 | (2006.01) |
| --- | --- |
| B01L 7/00 | (2006.01) |
| B01L 3/00 | (2006.01) |
| C12Q 1/686 | (2018.01) |
| C12Q 1/689 | (2018.01) |
| C12Q 1/6851 | (2018.01) |

(52) U.S. Cl.
CPC ......... *B01L 7/5255* (2013.01); *B01L 3/50851* (2013.01); *B01L 3/50853* (2013.01); *C12Q 1/686* (2013.01); *C12Q 1/689* (2013.01); *B01L 2200/0684* (2013.01); *B01L 2200/10* (2013.01); *B01L 2300/046* (2013.01); *B01L 2300/0654* (2013.01); *B01L 2300/0816* (2013.01); *B01L 2300/0829* (2013.01); *C12Q 1/6851* (2013.01); *C12Q 2600/158* (2013.01)

(58) Field of Classification Search
CPC ......... B01L 2200/0684; B01L 2200/10; B01L 2300/046; B01L 2300/0654; B01L 2300/0816; B01L 2300/0829; B01L 3/50851; B01L 3/50853; B01L 7/5255; C12Q 1/6851; C12Q 1/686; C12Q 1/689; C12Q 2600/158

See application file for complete search history.

(56) References Cited

FOREIGN PATENT DOCUMENTS

| JP | 2007061061 | * | 3/2007 |
| --- | --- | --- | --- |
| KR | 10-2004-0048754 A | | 6/2004 |
| KR | 10-2005-0041159 A | | 5/2005 |
| KR | 10-2006-0019700 A | | 3/2006 |
| KR | 10-0794699 B1 | | 1/2008 |
| KR | 10-0794703 B1 | | 1/2008 |
| KR | 10-2008-0103548 A | | 11/2008 |
| KR | 10-2010-0115186 A | | 10/2010 |
| KR | 10-1089045 B1 | | 12/2011 |
| KR | 10-2013-0065337 A | | 6/2013 |
| WO | WO 2010133257 | * | 11/2010 |

OTHER PUBLICATIONS

Zhang et al., 35, 13, 4223-4237, Jun. 2007.*
Kuangwen Hsieh et al. "Rapid, Sensitive, and Quantitative Detection of Pathogenic DNA at the Point of Care through Microfluidic Electrochemical Quantitative Loop-Mediated Isothermal Amplification" Angewandte Chemie, 2012, vol. 124, No. 20, pp. 4980-4984.

* cited by examiner

*Primary Examiner* — Cynthia B Wilder
(74) *Attorney, Agent, or Firm* — Novick, Kim & Lee, PLLC; Sang Ho Lee

(57) ABSTRACT

The present invention relates to an ultra-high speed real-time PCR device on the basis of a lab-on-a-chip for detecting bacteria that causes food poisoning pertaining to agricultural food and a food poisoning detection method using the same. The present invention can provide a micro PCR chip which can simultaneously accommodate a plurality of small-volume samples and concurrently secure maximum thermal contact efficiency with a heating block so as to secure rapid results, and accurately measure an optical signal emitted from a nucleic acid amplification product even without any separate filtering or processing. Further, on the basis of the PCR chip, the present invention can provide a real-time PCR device which can rapidly obtain a nucleic acid amplification result of which the reliability is secured even without a complicated light-signal measuring module.

19 Claims, 19 Drawing Sheets
Specification includes a Sequence Listing.

HIGH-SPEED REAL-TIME PCR DEVICE BASED ON LAB-ON-A-CHIP FOR DETECTING FOOD-BORNE BACTERIA TO AGRIFOOD, AND METHODS FOR DETECTING FOOD-BORNE BACTERIA TO AGRIFOOD USING THE SAME

TECHNICAL FIELD

The present invention relates to a micro PCR chip, including a primer set for detecting food-borne bacteria, a real-time PCR device comprising the same, and a method for detecting food poisoning by using the same.

BACKGROUND ART

Since the food-borne bacteria are primarily transmitted through foods such as meat, dairy products, drinking water, agricultural foods, etc., a method by which the presence or absence of the food-borne bacteria in samples such as food can be confirmed quickly and economically is required. Conventional methods for detecting food-borne bacteria are culturing the sample in a selective medium to separate the bacteria which are estimated as the food-borne bacteria, and then confirming them by biochemical or immunological methods. However, in the immunological method using an antibody, it is possible to detect bacteria with high accuracy, but it requires a large number of samples, and for the production of antibody required for each diagnosis, the protein purification of the relevant bacteria, production, or manufacture of peptide is essential, and high cost for producing the antibody is needed. Furthermore, in view of the nature of the protein, there are many difficulties in use and storage of it and it can only detect one type or a limited kind of bacteria at one time, and a longer time is consumed in culturing bacteria. To improve these drawbacks, the detection kits of the various bacteria using the PCR method have begun to be researched and developed. Detection kits using PCR method have been increased in light of the demands in various fields because of a high accuracy, simplicity, and rapidity.

In particular, the method of real-time PCR being recently often used is that there is an increased observation in the PCR amplification product in real time for each cycle of the PCR, and that detecting and quantitatively analyzing a fluorescent substance that reacts with PCR amplification products. This method has advantages, compared to that the existing PCR methods in which the gel was stained after finishing the final step to make electrophoresis in order to verify the PCR amplification product. The advantages include: no additional work for electrophoresis is needed, precision and sensitivity are excellent, it has high reproducible rate, and the automation is possible, the result can be digitized, it is rapid and simple, a biological safety according to detrimental problems such as UV irradiation and pollution by dyes such as EtBr (Ethidium Bromide) is excellent, and it is possible to automatically confirm the presence or absence of amplification of specific genes. Thus, rather than a qualitative result such as PCR or antigen/antibody via the method of real-time PCR, it is possible to confirm the quantitative results with high specificity. Further, since it is a probe labeled with a fluorescent label factor, it can confirm the results of a sample even with an amount smaller than the amount to be used for a DNA chip or antigen/antibody reaction. Therefore, in order to rapidly and accurately diagnose infection cause by food-borne bacteria in food, a need for the development of detection methods and detection kits of food-borne bacteria using real-time PCR method is in demand.

Real-time PCR (real-time Polymerase Chain Reaction) has been recently used a lot in the execution of a nucleic acid amplification reaction because of the advantage that a nucleic acid amplification product can be confirmed in real time during the reaction cycle without running the electrophoresis on gel. In general, an apparatus for carrying out the real-time PCR includes a thermal cycler with one or more heat blocks to perform a nucleic acid amplification reaction and a signal detector for measuring the signal generated from the nucleic acid amplification product in real time. Such signal detectors can be embodied as: a photo detector for detecting a fluorescence signal generated from the nucleic acid amplification products, an electronic signal detector for detecting an electric signal generated through a specific binding of the nucleic acid amplification product and the mediator interconnecting with it, and the like.

Meanwhile, in a recent medical field, effective diagnosis and treatment methods for implementing a personalized medicine (tailor-made medicines) have been actively developing, and in order to substantially achieve a personalized medicine, there is a need for rapid and accurate diagnosis and treatment for a number of objects. In this case, it could be said that in the diagnosis and treatment, the nucleic acid amplification step is the pre-process which is mostly based, and the real-time PCR which is an example for performing this is the pre-step in the realization of personalized medicine. However, since the real-time PCR has the assumption of a complex execution process, it takes considerable time to complete the step, and the devices for recognizing this are mostly expensive and large, and thus, there has been a failure to realize the potential of personalized medicine. Recently, many attempts have been made to solve said problems.

In this regard, Korean Patent Publication No. 10-2004-0048754 (Temperature-controllable, real-time fluorescence detection apparatus) provides a portable compact fluorescence detection device wherein various wavelengths of fluorescence are searched rapidly within a few seconds even at a low concentration of the sample sensitively, wherein the enzyme reactions can be searched and analyzed in real time at an more economical price. Specifically, the said fluorescence-searching apparatus is the device analyzing the sample by searching fluorescence emitted from a biological sample after irradiating a light source to said sample, characterized by comprising a LED array disposed so that a plurality of LEDs sequentially emit the light; a well chamber block having a plurality of wells to insert the sample vessel; a multi-channel PMT to detect fluorescence emitted from said sample by each LED light-emitting of said LED array; and a plurality of optical fibers to transmit fluorescence emitted from said each sample to said multi-channel PMT, in a fluorescence-searching apparatus comprising a sample vessel, light source locating so as to irradiate the sample vessel, fluorescence-transmitting device, wavelength selection device, and controlling unit.

Also, Korean Patent Registration No. 10-0794703 (Real-time monitoring apparatus of biochemical reaction) provides an apparatus which can compare and analyze the reaction degree of various samples, by minimizing light detection sensitivity deviation upon the reaction in a reaction tube plate. Specifically, the previous real-time monitoring apparatus comprises a temperature-regulating block system consisting of the heat transfer block for transferring heat to the reaction tube and the thermoelectric element being a heat source capable of supplying heat to the reaction tube; the irradiation source unit consisting of a lamp and a optical waveguide for irradiating uniform light to the sample in the reaction tube; and an optical system composed of a reflecting mirror for changing an optical path, and a light receiving unit for receiving the fluorescence generated from the sample of the reaction tube by the light irradiated by the irradiation source unit.

Also, Korean Patent Registration No. 10-1089045 (Real-time monitoring device of the nucleic acid amplification reaction product) whose purpose is to monitor the generation of a reaction product produced during the reaction while performing a nucleic acid amplification reaction such as the polymerase chain reaction for a large number of samples in small amounts, and provide a real-time monitoring device comprising a polarizer, polarization beam splitter, polarization converter, and the like.

Further, Korean Patent Publication No. 10-2008-0103548 (Real-time detection apparatus of nucleic acid amplification products) provides a real-time detection system of the nucleic acid amplification products that can determine the strength [DNA] real of a plurality of wells, without using a second fluorescence signal used for correction, in order that error factors on the device can be eliminated or reduced, by applying a temperature cycle to a plurality of wells, detecting fluorescence strength from a nucleic acid amplification product in each well in real time, and further fluorescence measurement values obtained from the well, [DNA] raw, and fluorescence measurement values obtained from the periphery of the connection wall near the well, [DNA] bg, and subtracting the fluorescence measurement value [DNA] bg from the fluorescence measurement value [DNA] raw.

Also, Korean Patent Registration No. 10-0794699 (real-time monitoring device of the nucleic acid amplification reaction product) provides a real-time monitoring device of the nucleic acid amplification reaction product, characterized by comprising a transparent sealing cover to cover reaction vessel and the reaction vessel having many wells to receive many samples for monitoring the generation of a reaction product produced during the reaction in real time while performing a nucleic acid amplification reaction such as the polymerase chain reaction, of a large number of samples in small amounts; fluorescence element consisting of selective transmitting filter located in front of excitation light source, the line polarizer for line-polarizing the light passed through the filter; light-receiving element consisting of line-polarizer located in the direction perpendicular to the line polarizer of the light-emitting element, light-collecting lens for collecting light passed through the line polarizer, selective transmitting filter transmitting the light passed the light-collecting lens, and fluorescent-sensing element.

However, since the above-mentioned prior art utilize a large number of measurement modules consisting of complex and sophisticated fluorescence signals in order to measure a number of the nucleic acid amplification products at the same time, the large size of the device and high cost are still problematic. Further, although said prior arts' purposes are measure a large number of small amounts of samples simultaneously, they do not disclose any method for solving the phenomenon in which the signal sensitivity is greatly reduced by a bubble which in the nucleic acid amplification process is generated by heating in a small amount of the sample solution contained in the small reaction vessel.

Therefore, a real-time PCR mounting apparatus is still needed that is capable of making real-time monitoring of nucleic acid amplification product at a low cost more quickly in order to ensure the reliability of the measured values along with the measuring of a large number of small amounts of nucleic acid amplification products at the same time, this is also applicable in regards to the detection device which can simultaneously, quickly, and accurately detect a plurality of food-borne bacteria, and the detection method of food-poisoning bacteria by using this.

DISCLOSURE

Technical Problem

The present invention is to provide a food poisoning detection device and method, which can simultaneously and quickly measure a large number of small amounts of nucleic acid amplification products, detect nucleic acid amplification products at a low cost, and further simultaneously, quickly, and accurately detect poisoning of agricultural food by utilizing a micro PCR chip through which reliability of the results can be secured.

Technical Solution

In order to carry out the challenge sought for solving the problem as mentioned above, one embodiment of the present invention provides a micro-Polymerase Chain Reaction (PCR) chip for detecting a food-borne bacteria, comprising a PCR reaction chamber wherein an upper portion is opened; and a cover having a light-transmitting element made of a light transmittable material that extends along the light path projected toward inside the PCR reaction chamber from some regions of closed sides faced on said opened upper portion, which comprises a primer set for detecting *Salmonella* spp. gene consisting of a primer containing 15 or more of sequential nucleotides of the base sequences of SEQ ID NO: 1 and a primer containing 15 or more of sequential nucleotides of the base sequences of SEQ ID NO: 2; a primer set for detecting *Listeria monocytogenes* gene consisting of a primer containing 15 or more of sequential nucleotides of the base sequences of SEQ ID NO: 3 and a primer containing 15 or more of sequential nucleotide of the base sequences of SEQ ID NO: 4; a primer set for detecting *Staphylococcus aurens* gene consisting of a primer containing 15 or more of sequential nucleotides of the base sequences of SEQ ID NO: 5 and a primer containing 15 or more of sequential nucleotides of the base sequences of SEQ ID NO: 6; and a primer set for detecting *Escherichia coli* gene consisting of a primer containing 15 or more of sequential nucleotides of the base sequences of SEQ ID NO: 7 and a primer containing 15 or more of sequential nucleotides of the base sequences of SEQ ID NO: 8, respectively.

According to one embodiment of the present invention, the above PCR reaction chamber can be made to have a liquid sample volume (receiving amount) of 10 μl or less. In this case, the PCR reaction chamber is capable of containing (receiving) 5~8 μl of liquid sample.

The light transmitting unit may be disposed at the center of the closed face.

The light transmitting unit may touch the bottom of the PCR reaction chamber, or may be placed at around a spaced location upward from the surface to the bottom of the PCR reaction chamber.

The said cover can further comprise a hole which surrounds through said light-transmitting portion, and a flexible packing unit for sealing the opened upper surface in contact with the opened upper surface of the PCR reaction chamber.

The said micro PCR chip for detecting the food-borne bacteria may be implemented to have a flat plate shape.

The micro PCR chip for detecting the food-borne bacteria may comprise the first plate in the form of a flat plate; the second plate in a flat form having said PCR reaction chamber, disposed on the upper side of the first plate; and the third plate disposed on the upper side of the second plate, which is faced on the opened upper face of the PCR reaction chamber to seal the opened upper plate, and can perform the role of cover having said light transmitting unit. In this case, it can further comprise the hole surrounding so as to penetrate the light-transmitting portion between the second and the third plates, and the flexible packing unit sealing the opened upper side, which is faced on the upper face of the PCR reaction chamber.

It may further include a heat-releasing unit that is mounted so as to release heat generated from the PCR reaction chamber to the outside.

Another embodiment of the present invention provides a real-time PCR apparatus, which comprises a micro PCR chip for detecting the above food-borne bacteria; one or more of heat block component mounted in thermal contact with at least one surface of the micro PCR chip for detecting the food-borne bacteria; and a light-detecting module which is implemented to detect a optical signal generated from the PCR amplified product in the PCR reaction chamber of a micro PCR chip for detecting the food-borne bacteria.

Yet another embodiment of the present invention provides a real-time PCR apparatus, which comprises of the micro PCR chip for detecting the food-borne bacteria; the first heat block component embodied so as to dispose on a substrate, but to be in heat-contact with the micro PCR chip; the second heat block component embodied so as to be disposed in the state being spaced apart from the first heat block on said substrate; the chip holder which can be moved from left to right and/or from up to down over the first and second heat block components by the driving means and the micro PCR chip is equipped therewith; and a light-detecting module which is implemented to detect a optical signal generated from the PCR amplification product of the PCR reaction chamber of the micro PCR chips during movement between said first heat block component and the second heat block component.

Advantageous Effects

According to the means to solve the problems described above, it is possible to simultaneously and rapidly measure a number of small amounts of nucleic acid amplification product, and to detect the nucleic acid amplification products at a low cost, and further to simultaneously, quickly and accurately detect whether food poisoning of agricultural food by utilizing a micro PCR chip through which the reliability of the results can be secured.

BEST MODE FOR INVENTION

Figure 1:
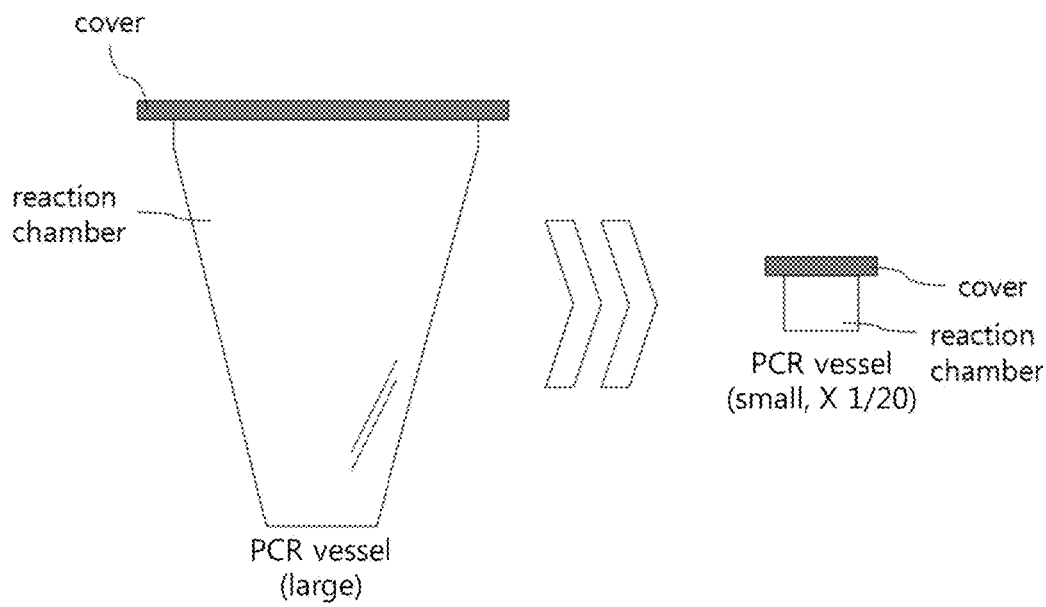
FIGS. 1-3 relate to a phenomenon that the sensitivity of the optical signal by a bubble generated during the PCR process inside the extremely miniaturized PCR vessels (small, ×1/20) is reduced in comparison with that of the conventional PCR vessels (large).

Hereinafter, with reference to the accompanying drawings, Examples according to the present invention will be described in detail. The following description is only a means to easily understand the examples of the present invention and is not intended to limit the scope of the present invention.

Examples of the present invention relate to a real-time PCR monitoring Polymerase Chain Reaction (PCR), and more particularly the nucleic acid amplification reaction in real time.

PCR is a technique for amplifying a nucleic acid having the specific base sequence sites exponentially by repeatedly heating and cooling the PCR sample and reagent comprising a nucleic acid to replicate the specific base sequence site of the nucleic acid in a chain reaction, which is currently widely used for diagnosis and analysis of the diseases in a life science, genetic engineering, the medical fields, and the like. PCR apparatus for performing PCR efficiently has been variously developed recently. A PCR apparatus is commonly referred to as a device that is implemented to perform PCR to amplify a nucleic acid having a specific nucleotide sequence. Generally, A PCR device performs a denaturing step heating PCR sample and reagents comprising a double stranded DNA at the particular temperature, for example, about 95° C. to separate a double stranded DNA to a single stranded DNA; an annealing step providing an oligonucleotide primer having a sequence complementary to the specific base sequence to be amplified to the PCR sample and reagents and cooling to the specific temperature, for example, 55° C., along with the separated, single-stranded DNA to bind to the oligonucleotide primer to a particular base sequence of the single stranded DNA to form a partial DNA-primer complex; and after the annealing step, an extension (or amplification) step maintaining the PCR sample and reagents at the activation temperature of the DNA polymerases, for example 72° C. to form the double stranded DNA based on the primer of the partial DNA-primer complex by DNA polymerase, wherein the said extension (or amplification) step is repeated, for example, 40 times 20 times so as to be able to amplify the DNA having said specific base sequence exponentially. On the other hand, recently PCR apparatuses can perform said annealing step and the extension (or amplification) step at the same time, and in this case, the above PCR device may also complete the first cycle by performing two steps consisting of said annealing and extension (or amplification) steps following the denaturation step.

Real-time PCR means a nucleic acid amplification reaction that a measuring device such as, for example, a fluorescence photometer (optical system) module is applied to a thermal cycler used for PCR to be able to monitor the procedure that the product is generated. Real-time PCR, unlike a typical PCR, does not need an electrophoresis to confirm nucleic acid amplification products, and thus, has an advantage that it is possible to analyze a nucleic acid amplification product in real time accurately and quickly. Accordingly, recently the real-time PCR apparatus has also been actively developed, and in order for the real-time PCR device to sufficiently exhibit the advantage as described above, it should be made so as not to only increase the efficiency of the heat circulator, but also measure the optical signal generated from the amplification product accurately without errors.

Figure 2:
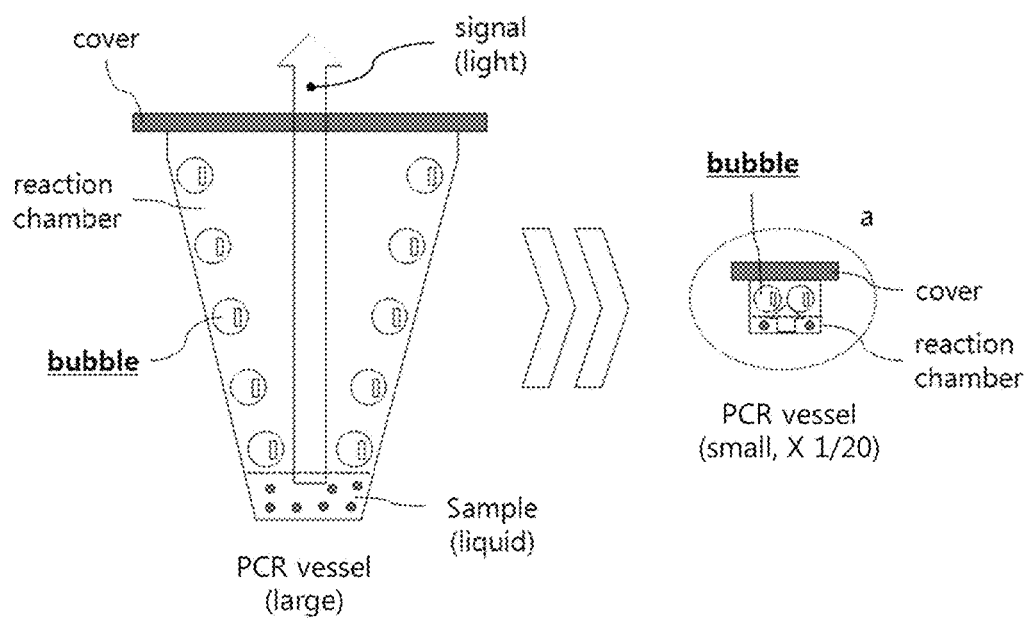
Figure 3:
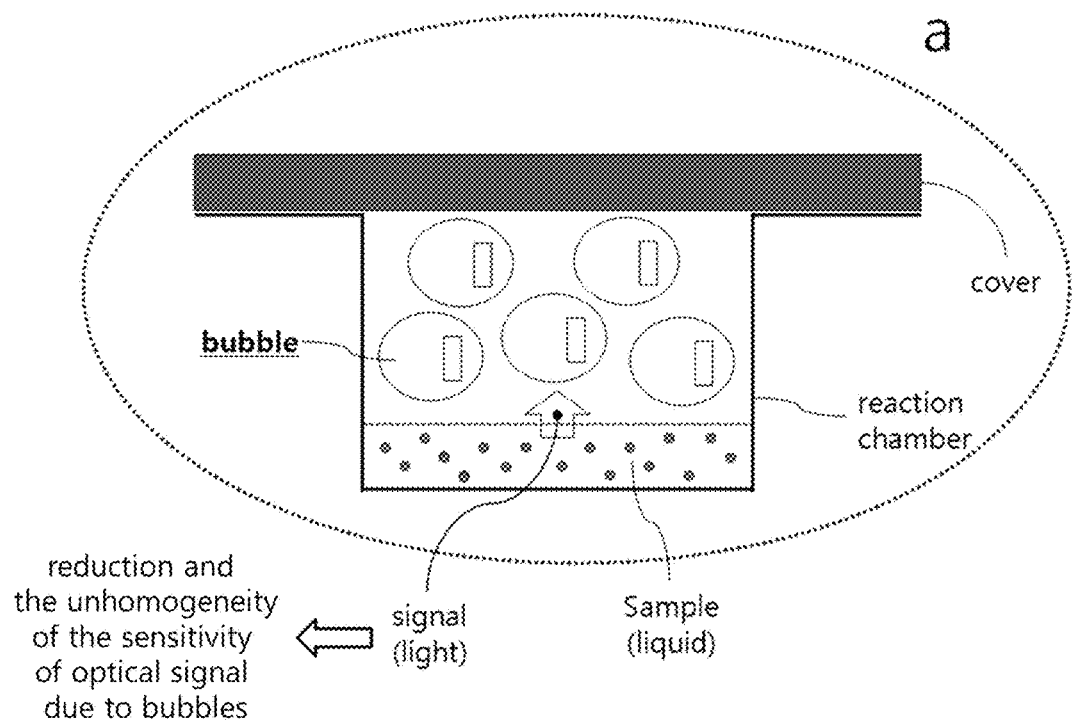

FIGS. 1-3 relate to the phenomenon that the sensitivity of the optical signal by a bubble generated during the PCR process inside the conventional PCR vessel (large) and the extremely-miniaturized PCR vessels (small, ×1/20) is reduced.

For substantial realization of customized medical services, recently PCR apparatuses are directed to a miniaturization, portability, rapidity, and economy. An existing PCR apparatus has problems because it is large not only in the vessel containing the PCR samples and reagents but also in the apparatus itself, and thus, has difficulty in the use and operation thereof and also presented difficulties in regards to partability. Since it wastes PCR samples and reagents considerably, the cost is also significantly consumed. Moreover, since the amounts of PCR samples and reagents to be used in the apparatus are high, it takes considerable time, and thus it is difficult to achieve an efficient PCR.

According to FIG. 1, the left panel is a conventional PCR vessel generally used (large), the right panel shows a PCR vessel (small) in which a size and a capacity of a liquid sample are extremely downsized (×1/20), relative to the PCR vessel (large). In general, the conventional PCR vessel (large) was composed of a reaction chamber to put PCR sample and reagents and its cover, the reaction chamber and cover were embodied as a light transmitting material, and PCR was carried out under the circumstance that the vessel has a liquid sample capacity (volume) of about 200 μl and contained about 20 μl of the sample and reagents. The above PCR vessel (small) was composed of a reaction chamber to put the PCR sample and reagents and its cover, and the reaction chamber and the cover may be embodied as the light transmitting materials, and in this case, the PCR vessel (small) had the liquid sample capacity of about 10 μl, and PCR was carried out under the circumstance that the vessel had a liquid sample capacity of about 10 μl and contained about 5~8 μl of the sample and reagents. Thus, a manufacturing of the extremely downsized PCR vessel can be easily embodied in the currently known technology area. However, since the miniaturization of the PCR vessel gives significant adverse effects, as described below, in the measurement of nucleic acid amplification products, it is difficult to be easily embodied.

According to FIG. 2, a phenomenon that the optical signal sensitivity is decreased due to the bubble that occurred during the PCR process inside the extremely-miniaturized PCR vessel (small, ×1/20) relative to the conventional PCR vessel (large) can be confirmed easily. As mentioned above, PCR entails the step for supplying the heat, a significant amount of bubbles is generated by heating the liquid samples inside the PCR vessel, and such bubbles cut off the optical signals generated from a nucleic acid amplification product. On the other hand, according to FIG. 2, although the bubbles generated from the interior of the above PCR vessel (large) reduce the optical signal sensitivity by blocking the optical signals generated from the nucleic acid amplification products, since the internal space of the vessel is sufficiently larger, relative to the size and number of bubbles per se, the above bubble is either dispersed inside the above PCR vessel (large) or forms a cluster on the inner wall of the PCR vessel (large), and thus, it is not impossible to measure the optical signal, though the optical signal sensitivity is reduced. However, according to FIG. 3 enlarging a portion of "a" in FIG. 2 and FIG. 2, since the bubbles generated from inside the above PCR vessel (small) considerably lower the sensitivity of the optical signal and make it be ununiformity by blocking the optical signals generated from the nucleic acid amplification product, due to the fact that the inner space of the reaction vessel is considerably smaller, relative to the number and size of the bubble itself, the reliability of the results is lowered. Therefore, when the PCR device is miniaturized and simultaneously the miniaturization of the PCR vessel mounted on it is embodied, ways to ensure the reliability of results due to the reduction and non-uniformity of the sensitivity of the optical signals correspondingly need to be sufficiently considered.

Figure 4:
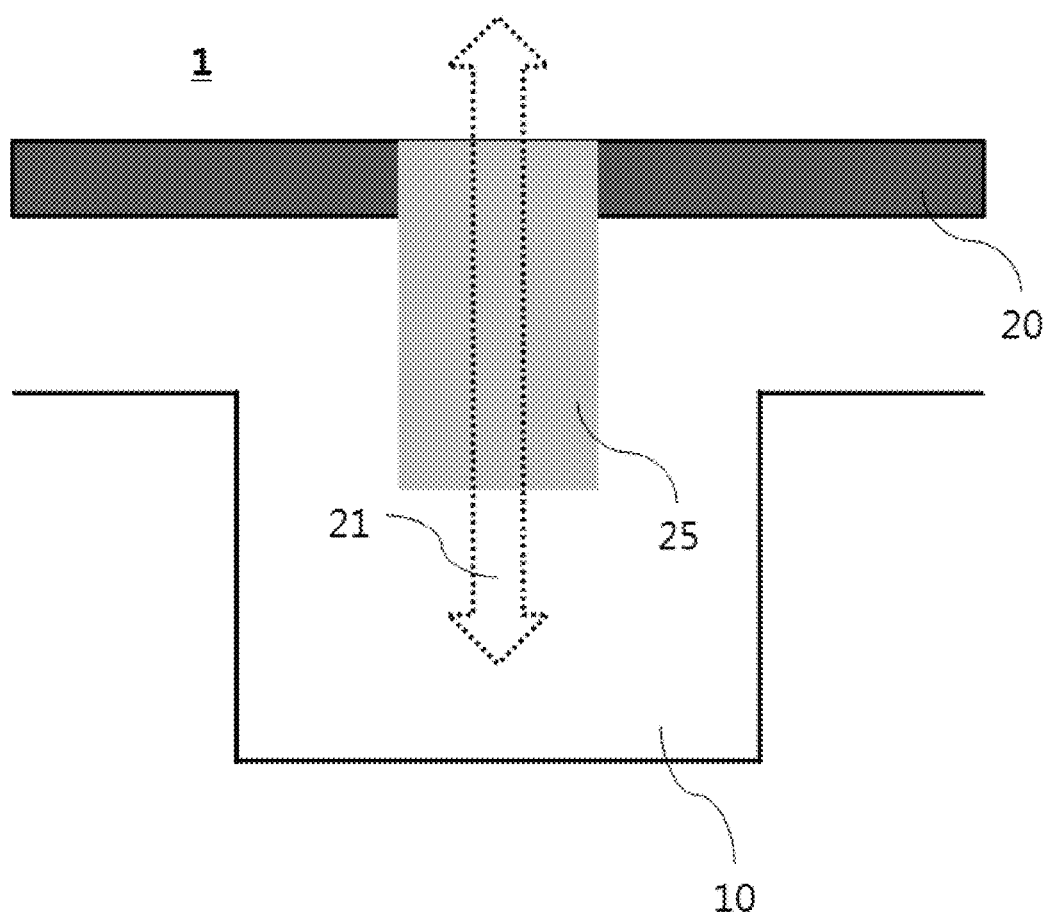
FIG. 4 relates to a cross-sectional view regarding the basic structure of a micro PCR chip according to an embodiment of the present invention.

FIG. 4 relates to a cross-sectional view regarding the basic structure of a micro PCR chip according to an embodiment of the present invention.

According to FIG. 4, Micro-Polymerase Chain Reaction Chip (Micro-PCR Chip) (1) according to an embodiment of the present invention comprises PCR reaction chamber (10) having the opened upper end surface; and a cover (20) with a light transmitting portion (25) made of the light transmitting material which is protruded from the part of the area of the sealed surface in contact with said opened upper surface toward the interior of the PCR reaction chamber (10) but is extended along an optical path (21).

The above PCR reaction chamber (10) is embodied to receive a liquid sample, i.e., PCR samples and reagents by opening the upper end surface but closing the bottom surface and the side edge surface. The above PCR reaction chamber (10) is to be embodied not to be affected by the repeated heating and cooling during the PCR procedure, and if it is possible to maintain such functions, it is not limited to the particular shape and/or material. Provided that, since the micro PCR chip (1) according to an embodiment of the present invention is based on the measurement of real-time optical signal of the nucleic acid amplification product, it is preferable that at least the portion superimposed on the optical path (21) is embodied as the light-transmitting material.

The cover (20) is in contact with the opened upper surface of the PCR reaction chamber (10) to play a role closing the above opened upper surface. The cover (20) plays a role not to flow out the PCR sample and reagents reacting in the interior of the PCR reaction chamber (10) and to maintain the internal temperature of the above PCR reaction chamber (10) by closing the opened upper surface of the PCR reaction chamber (10). On the other hand, the cover (20), if it is possible to embody the functions described above, may be embodied in various shapes and/or materials. Provided that, since the micro PCR chip (1) according to an embodiment of the present invention is based on the measurement of real-time optical signal of nucleic acid amplification products, it is preferable to be embodied as the light-transmitting materials.

Figure 6:
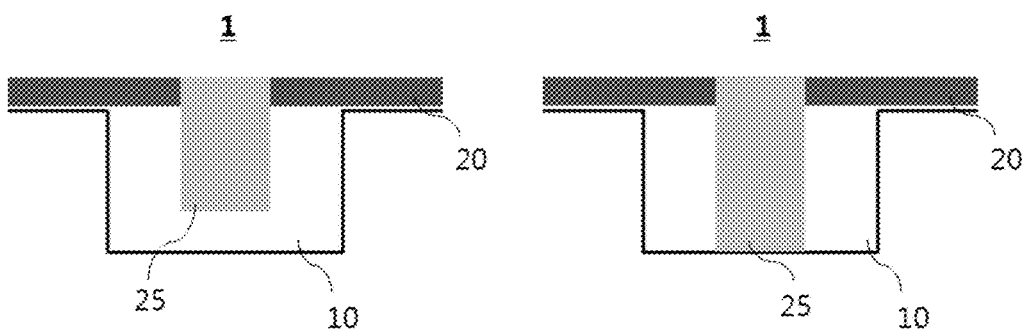
FIG. 6 relates to various types of light-transmitting portions of the micro PCR chip according to an embodiment of the present invention.

On the other hand, according to FIG. 4, the cover (20) is equipped with a light transmitting portion (25) made of the light transmitting material which is protruded from the part of the area of the closed surface in contact with said opened upper surface toward the interior of the PCR reaction chamber (10) but is extended along an optical path (21). The light transmitting portion (25) is the part that is embodied as the light transmitting material and to be extended along the optical path (21) for the measurement of the nucleic acid amplification products, and the optical signal generated from the nucleic acid amplification product in the interior of the said PCR reaction chamber (10). Further, the light transmitting portion (25) is embodied to be protruded from the sealed surface in contact with the opened upper surface of the PCR reaction chamber (10), i.e. a part of a region of the lower end surface of the cover (20) toward the interior of the PCR reaction chamber (10). Although the protrusion shape of the light transmitting portion (25) may be varied, it is preferable to be embodied as a cylinder or square pillar shape. In addition, according to FIG. 6, the protrusion shape of the light transmitting portion (25) can be embodied variously, and thus, it may be embodied to contact the bottom surface of the PCR reaction chamber (10) (right in FIG. 6), or it may be embodied upwardly from the bottom surface of the PCR reaction chamber (10) to some spaced position (left in FIG. 6). That is, the light transmitting portion (25) may be adjacent to or in contact to the surface of the liquid sample, or further, may be passed on the surface of the liquid samples to put into the interior of the liquid sample. In addition, if the light transmitting portion (25) is embodied so as to be extended along the optical path, it can be embodied on the closed surface in contact with the opened upper surface of the PCR reaction chamber (10), i.e. on any portion of the lower end surface of the cover (20), and it is preferable to be disposed in the central region of the closed surface, i.e., the central region of the lower end surface of the cover (20). On the other hand, although the capacity of the liquid sample of the PCR reaction chamber (10) is not limited to the specific volume, it is preferable to be embodied to have 10 μl or less of liquid sample capacity and to be embodied to receive 5~8 μl of the liquid sample.

Figure 5:
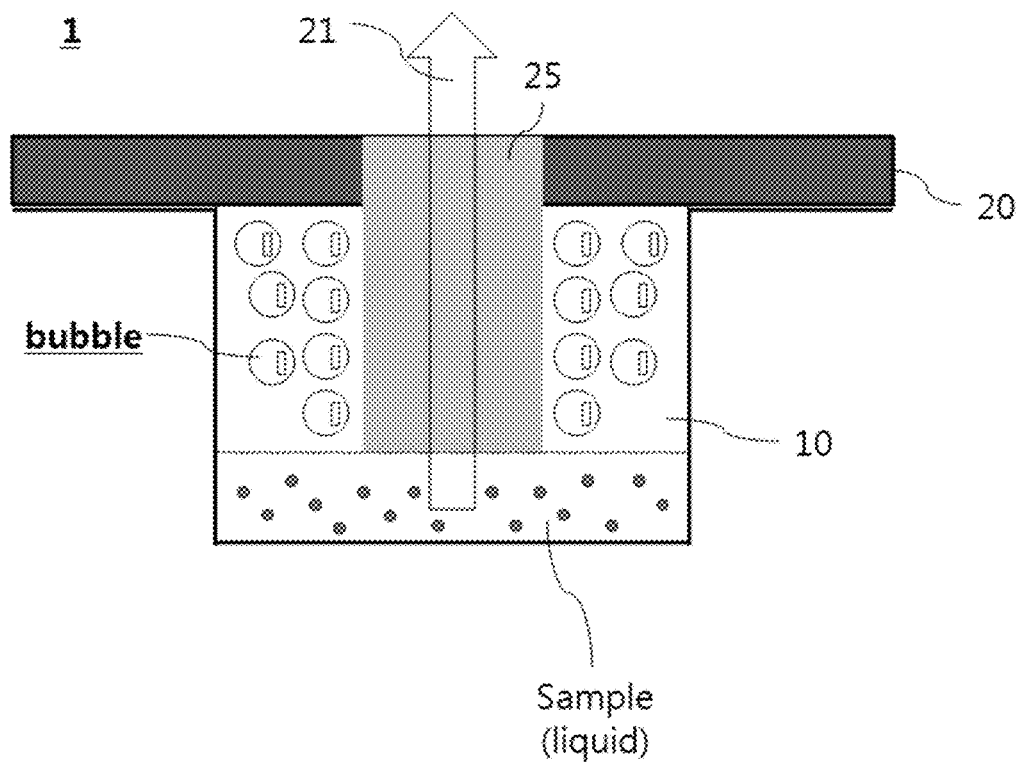
FIG. 5 relates to a principle that the optical signal from the PCR product is released, without any effect of the bubble generated during the PCR process inside the micro PCR chip according to an embodiment of the present invention.

FIG. 5 relates to a principle that the optical signal is emitted from PCR product, without any effect due to the bubble generated during the PCR process in the interior of Micro PCR chip according to an embodiment of the present invention.

As a PCR process proceeds, the internal PCR vessel liquid sample is heated and thus bubbles may occur accordingly, as previously described.

According to FIG. 5, when the liquid sample, i.e., PCR samples and reagents in the interior of the PCR reaction chamber (10) of the micro PCR chip (1) according to one embodiment of the present invention are heated by the heat supply, bubbles are generated. However, in the case of the micro-PCR chip (1) according to the embodiment of the present invention, the bubbles formed in the PCR reaction chamber (10) by the light transmission part (25) that is protruded from the lower surface of the cover (20), i.e., is protruded from the part of the area of the sealed surface in contact with said opened upper surface of the PCR reaction chamber (10) (according to FIG. 5, the central area) toward the interior of the PCR reaction chamber (10) but is extended along an optical path (21) are compressed and disposed in the peripheral space by being swept into the peripheral area of the edge surface of the light transmission portion (25). Accordingly, the bubbles are completely disengaged the optical signal path (light transmission portion, 25) formed from the nucleic acid amplification products presented in the liquid sample optical signal path (light transmission portion, 25), and never affect the optical signal sensitivity for measuring the nucleic acid amplification product. Therefore, when measuring the nucleic acid amplification product in real time in the real-time PCR process by using the micro-PCR chip (1) according to one embodiment of the present invention, since it never receives any effect of bubbles generated in the interior of the PCR reaction chamber (10), the optical signal sensitivity is increased considerably. As a result, by the micro PCR chip (1) according to one embodiment of the present invention, since the capacity of the liquid sample can be significantly reduced, for example, to below 10 μl, the PCR vessel can be extremely-microminiaturized, and simultaneously the optical signal sensitivity can be significantly increased, the miniaturization and portability of PCR vessel and real-time PCR apparatus can be achieved, and further a large number of small quantities of a nucleic acid amplification product can be quickly and accurately measured at the same time.

Figure 7:
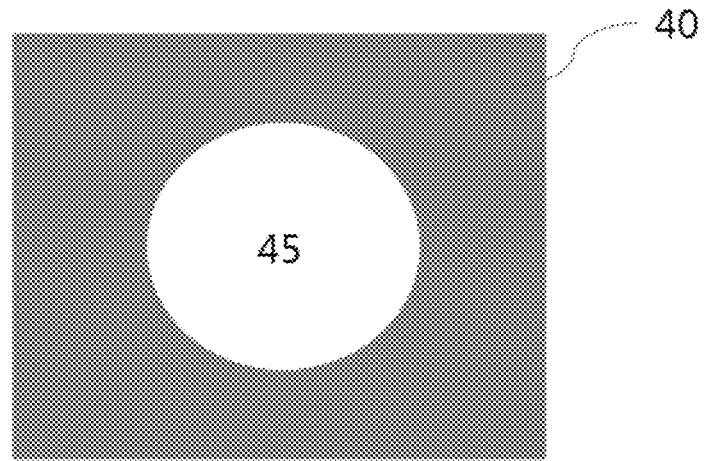
FIGS. 7-9 relate to a flexible packing part of the micro PCR chip according to an embodiment of the present invention.
Figure 8:
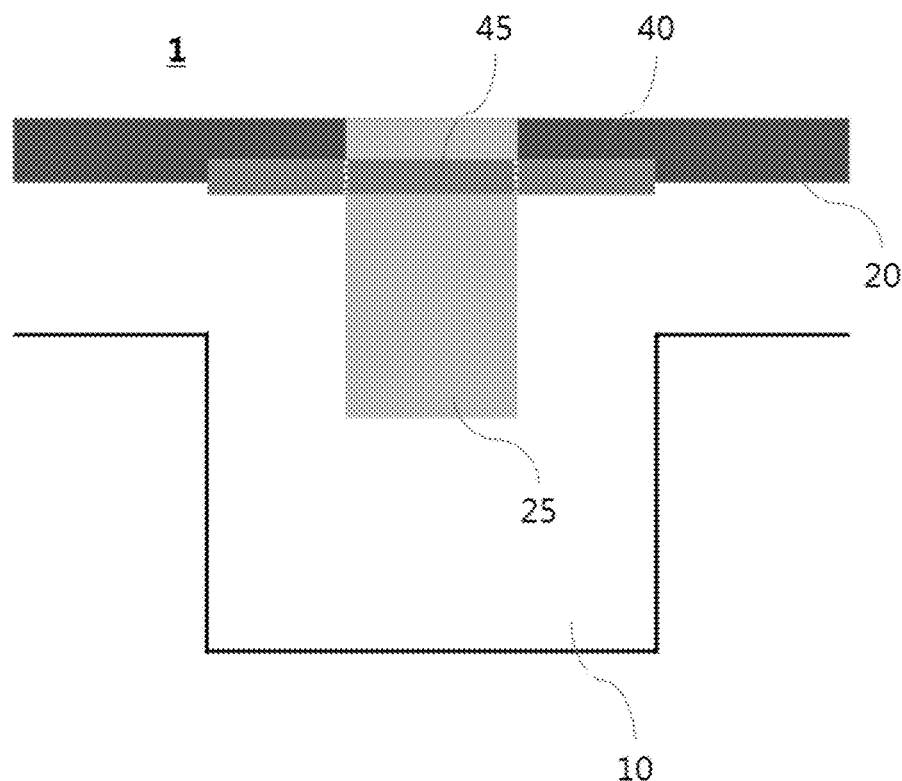
Figure 9:
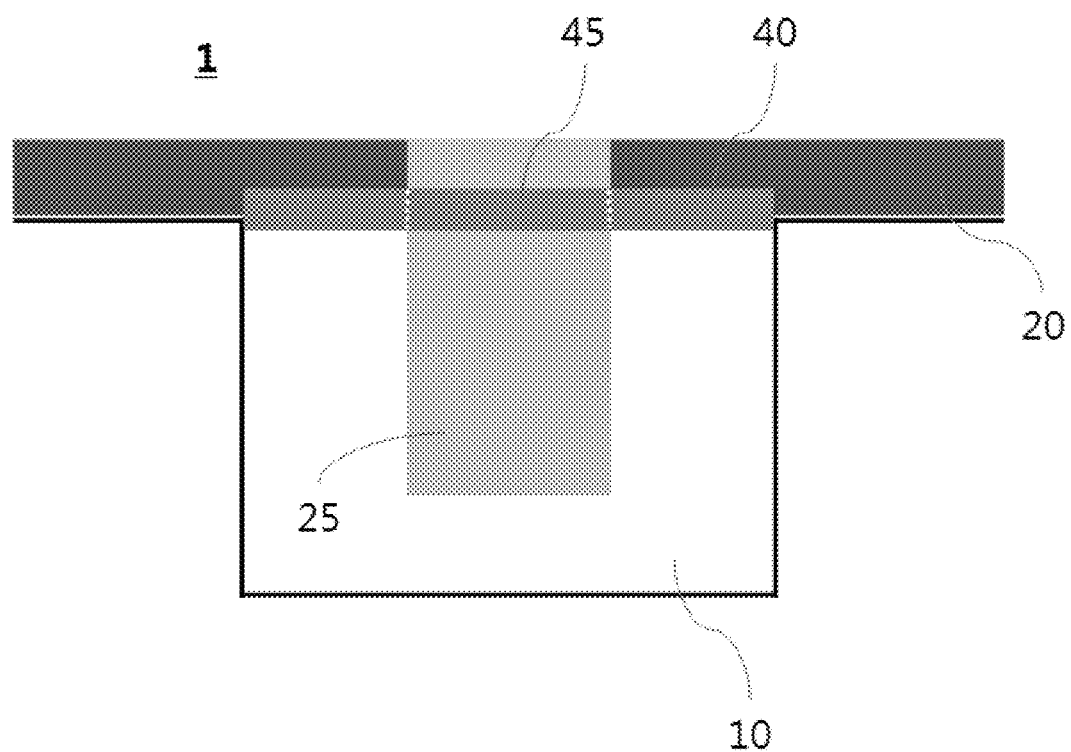

FIGS. 7-9 relate to a flexible packing part of the micro PCR chip according to an embodiment of the present invention.

According to FIGS. 7-9, the cover (20) of the micro PCR chip (1) according to an embodiment of the present invention further comprises the hole (45) which surrounds through the light transmission portion (25), and the a flexible packing part (40) which is in contact with the opened upper end surface of the PCR reaction chambers (10) to close the opened upper end surface.

The flexible packing part (40) plays a role to prevent the leak of the liquid sample by generating the bubbles or increasing a pressure due to the increasing of the internal temperature of the PCR reaction chamber (10). The flexible packing part (40) is embodied as a material having elasticity and stretchability such as rubber or silicone to buffer the expansion force caused by generating the bubble or increasing of the pressure, but to maintain a sealed state of the PCR reaction chamber (10). On the other hand, since the hole (45) is embodied according to the shape of the light transmission portion (25), although it has been embodied as being circular in FIG. 7, it is not limited thereto. On the other hand, FIG. 8 shows a state in which the flexible packing part (40) is attached to said cover (20), but surrounds through the light-transmitting portion (25), and FIG. 9 shows the state sealing interior space of the PCR reaction chamber (10) by attaching the cover (20) in the state of FIG. 8 to the upper end surface of the PCR reaction chamber (10).

Figure 10:
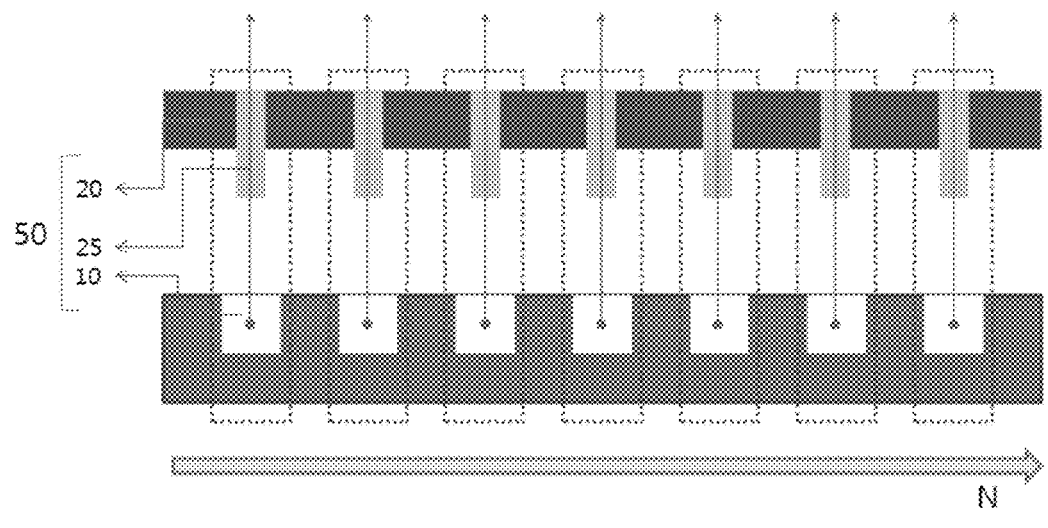
FIG. 10 relates to a micro PCR chip according to an exemplary embodiment of the present invention wherein a PCR reaction chamber and a unit module that includes a cover comprising a light-transmitting portion are repeatedly implemented two or more times.

FIG. 10 relates to a PCR reaction chamber, and a micro PCR chip according to an embodiment of the present invention in which a unit module comprising a cover equipped with a light-transmission portion is repeated two or more times.

As described above, since the micro PCR chip (1) according to an embodiment of the present invention can be extremely-microminiaturized without considerably increasing the sensitivity of the optical signal by the PCR reaction chamber (10) and the cover (20) equipped with the light transmitting portion (25), it is possible to embody a PCR vessel having a multi-chamber structure receiving a large number of small amount of liquid samples.

According to FIG. 10, the micro PCR chip (1) according to an embodiment of the present invention can include two or more of the PCR reaction chamber (10) and the unit module (50) composed of the said cover (20). For example, as shown in FIG. 10, if the micro PCR chip (1) is embodied as the flat plate shape, since it can be embodied as two or more numbers (N) by displaying it in a row or by integrating it in a plate shape of a circular space, and thus for example, the above unit module (50) can be embodied as 19 pieces (19 well), 48 pieces (48 well), 96 pieces (96 well), etc.

Figure 11:
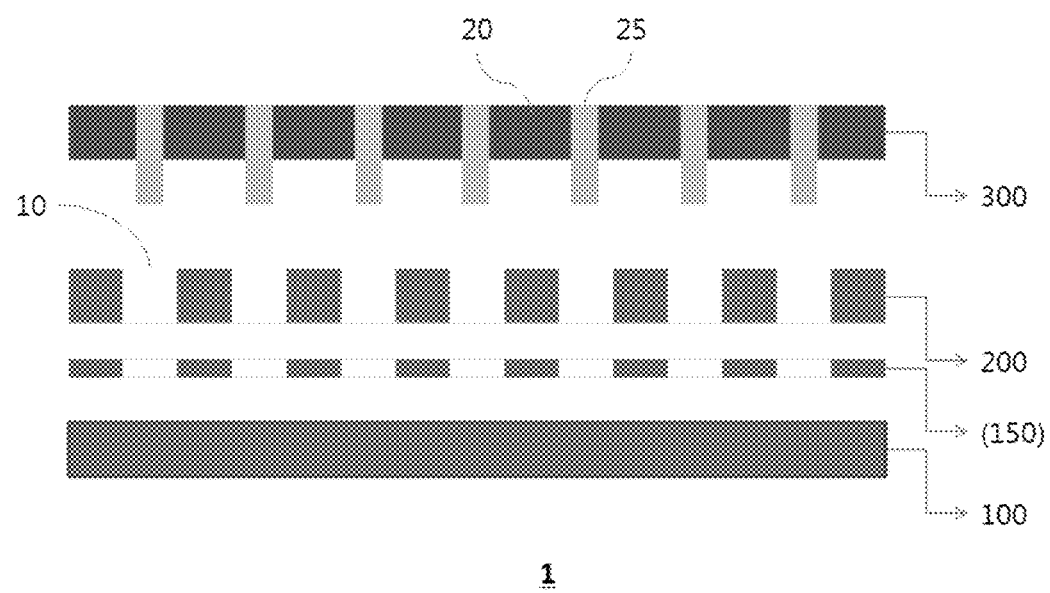
FIGS. 11-12 relate to a cross-sectional exploded view of a micro PCR chip according to an embodiment of the present invention.
Figure 12:
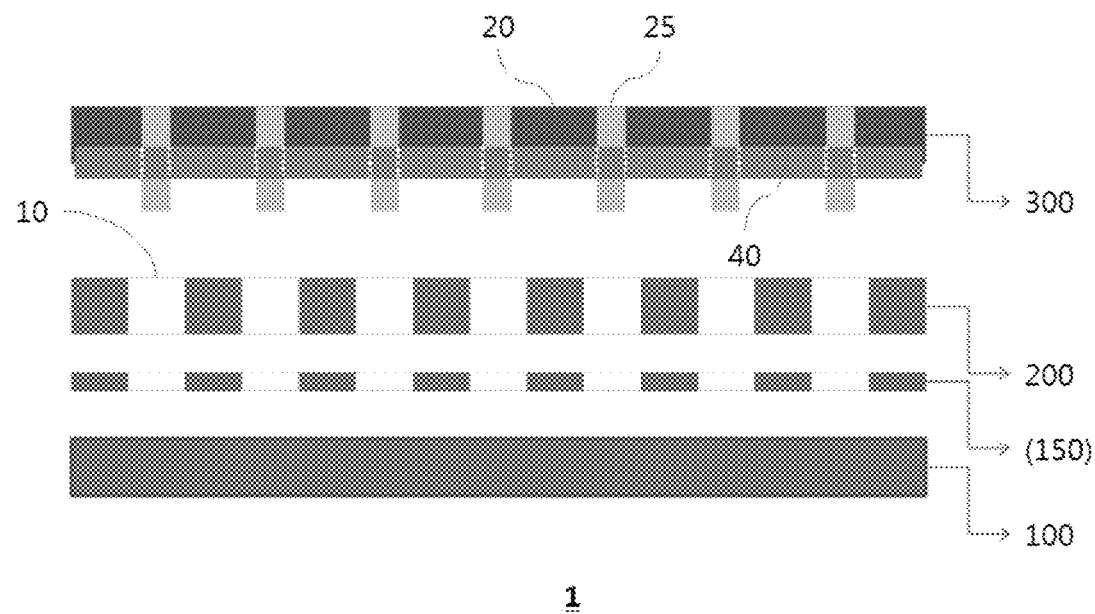

FIGS. 11-12 relate to a cross-sectional exploded diagram of a micro PCR chip according to an embodiment of the present invention.

According to FIG. 11, the micro PCR chip (1) according to one embodiment of the present invention can be embodied to comprise the first plate (100) in flat plate shape; the second plate (200) equipped with the PCR reaction chamber (10), as disposed on the upper of the first plate (100); and the third plate (300) which closes the opened upper surface of the PCR reaction chamber (10) by attaching to the opened upper surface of it, but plays the role of the cover (20) equipped with the light transmission portion (25).

The first plate (100) is embodied as a flat plate shape, and plays a role of the bottom support of the micro PCR chip (1) according to one embodiment of the present invention. The first plate (100) can be embodied as various materials, but when considering the cost reduction, it is embodied as plastic materials, such as polycarbonate (PC), polyethylene terephthalate (PET) and the like, and it is desirable to be embodied as the material transmitting the light. In addition, the surface of the first plate (100) can be variously embodied, but it is preferable to be treated to have a hydrophilic surface. In addition, the first plate (100) may be preferably embodied as about 0.03 to 1.0 mm, and more preferably as about 0.1 to 0.5 mm.

The second plate (200) is embodied as a flat plate shape, and plays a role forming a region of the PCR reaction chamber (10) of the micro PCR chip according to an embodiment of the present invention. The second plate (200) can be embodied as various materials, but when considering the cost reduction, it is embodied as the plastic materials, such as polycarbonate (PC), polyethylene terephthalate (PET) and the like, and it is desirable to be embodied as the material transmitting the light. In addition, the second plate (200) can be preferably embodied as about 0.5 to 5 mm, and more preferably about 1 to 2 mm.

On the other hand, according to FIG. 11, an additional layer (150) forming a bottom space of the PCR reaction chamber (10) of the micro PCR chip (1) according to one embodiment of the present invention can be formed between the first plate (100) and the second plate (200). This may be the conjugation surface between the first plate (100) and the second edition (200), or an adhesive layer. Thus, the surface between the first plate (100) and the second plate (200) can be adhered by the thermal adhesion, ultrasonic adhesion, UV adhesion, solvent adhesion method. In addition, the additional layer (150) may be preferably embodied as about 0.03 to 1.0 mm, and more preferably about 0.1 to 0.5 mm.

The third plate (300) is embodied as a flat plate shape, but is disposed on the upper of the second plate (200) and plays a role of the cover (20) which closes the opened upper surface of the PCR reaction chamber (10) of micro PCR chip (1) according to an embodiment of the present invention by attaching to the open upper surface of it, but is equipped with the light transmission portion (25). The third plate (200) can be embodied as the various materials, but when considering the cost reduction, it can be embodied as plastic materials, such as polycarbonate (PC), polyethylene terephthalate (PET) and the like, and it is preferable to be embodied as the material transmitting the light. In addition, the third plate (200) can be preferably implemented as about 0.5 to 5 mm, and more preferably as about 1 to 2 mm.

On the other hand, according to FIG. 12, the third plate (300) can include a hole surrounding to penetrate the light transmission portion (25) between the second plate (200) and the third plate (300), and the flexible packing part (40) which is in contact with the opened upper surface of the PCR reaction chambers (10) to close the opened upper surface. The flexible packing part (40) plays a role for preventing the leak of PCR sample and reagents being received the interior of the PCR reaction chamber (10) and the contamination in plural chambers. The flexible packing part (40) can be embodied as the various materials with elasticity stretchability, but it is preferable to be embodied as silicone, teflon and the like, for example. In addition, the flexible packing part (40) can be preferably embodied as about 0.1 to 2 mm, and more preferably about 0.5 to 1 mm, and the diameter of the circular hole can be embodied as about 1.0 mm.

Figure 13:
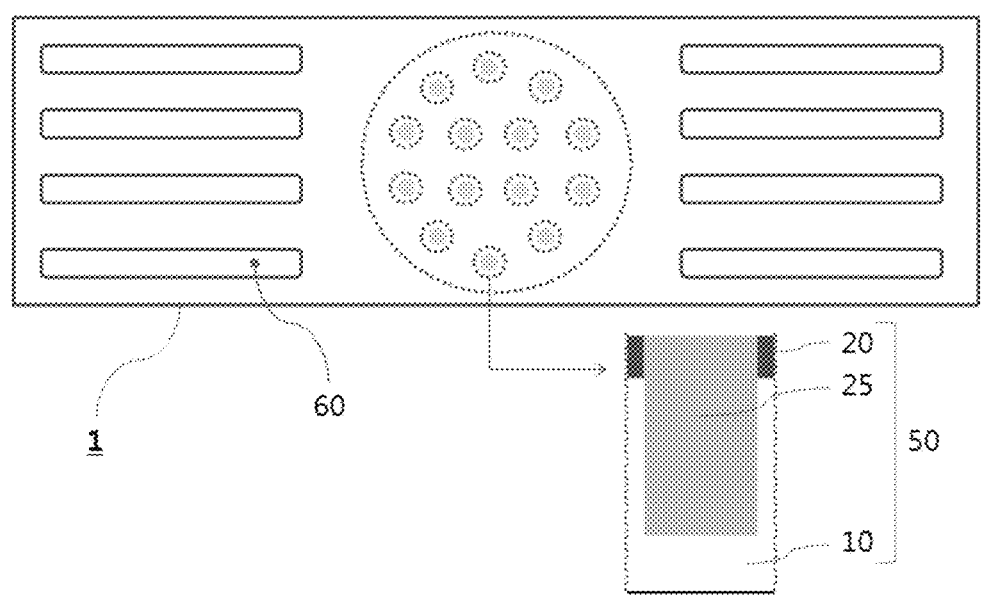
FIG. 13 relates to a micro PCR chip according to an embodiment of the present invention, comprising a heat-releasing part.

FIG. 13 relates to the micro PCR chip according to an embodiment of the present invention comprising a heat discharging portion.

Micro PCR chip (1) according to one embodiment of the present invention can further comprise the heat emitting portion which is embodied to emit the heat generated from the PCR reaction chamber (10) to the outside. According to FIG. 13, a micro PCR chip (1) according to an embodiment of the present invention is embodied for a plurality of unit modules (50) to be integrated in the central circular region, as the totally thin flat shape. As described above, since the high-temperature heat is generated in the interior of the PCR reaction chamber (10) in the above unit module (50) during the PCR process, when considering the reaction stability and heat resistance of equipment, the micro PCR chip (1) according to an embodiment of the present invention can dispose a heat discharging section (60) on both sides of said central circular region.

Figure 14:
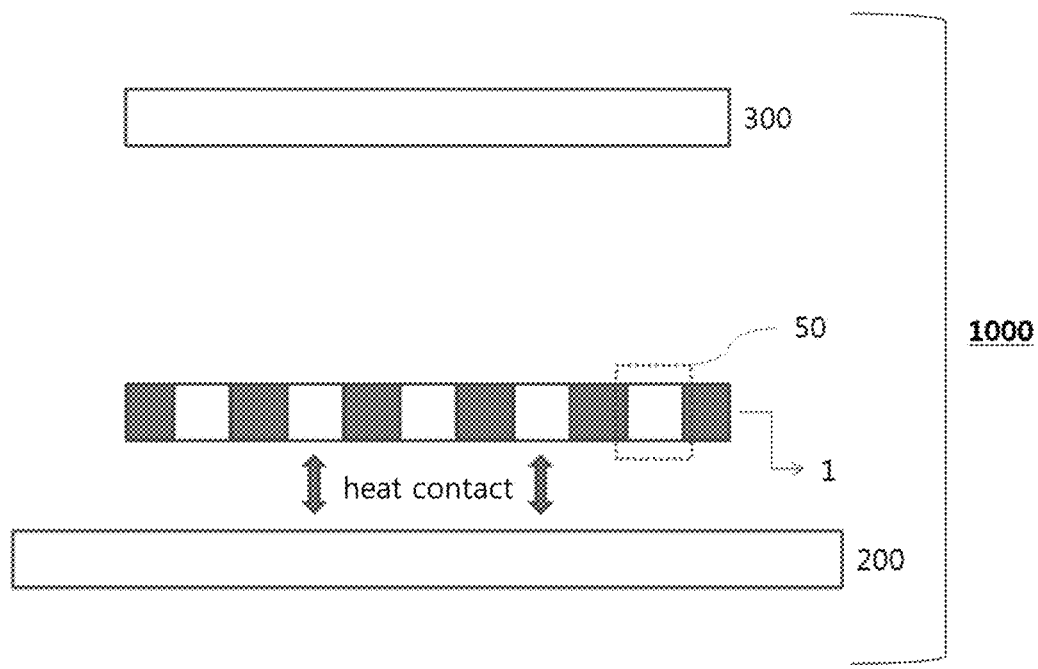
FIGS. 14-15 relate to a real-time PCR apparatus according to another embodiment of the present invention, which comprises a micro PCR chip according to an embodiment of the present invention, the heat block which is heat-contacted with the micro PCR chip, and a light-detecting module which is implemented to detect a optical signal generated from the PCR amplified product inside the PCR reaction chamber of the micro PCR chip.
Figure 15:
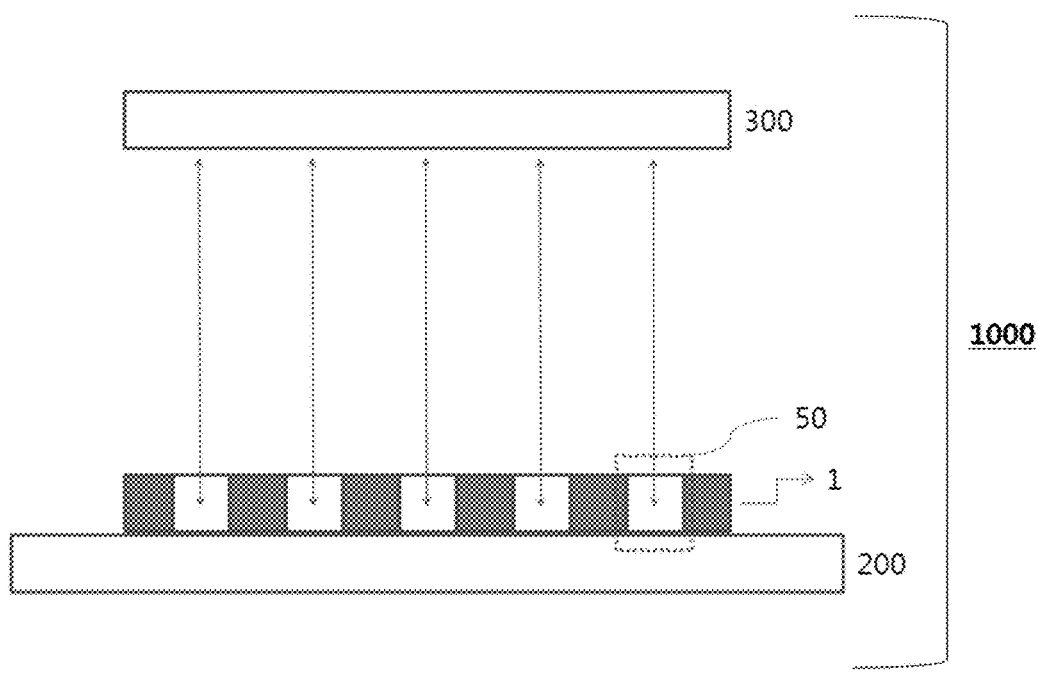

FIGS. 14-15 show the real-time PCR apparatus comprising a single heat block to which the micro PCR chip according to an embodiment of the present invention is applied.

According to FIGS. 14-15, the real-time PCR apparatus (2000) according to another embodiment of the present invention comprises the micro PCR chip (1) according to an embodiment of the present invention described above; one or more of heat block (200) embodied to be contacted with at least one surface of the micro PCR chip (1); and a light-detecting module (300) which is embodied to detect an optical signal generated from the inside of the PCR amplification product of the PCR reaction chamber (10) of the micro PCR chip (1).

The heat block (200) is the module that is embodied so that the heat exchange can be made by thermal contacting it with micro PCR chip (1). The heat block (200) may be embodied as the various materials, and in order to measure the optical signal of the nucleic acid amplification products, it may also be embodied so as to be generally (or partially) light-transmissible. The transparent heating element is comprised of materials having optical transparency and can include all substances having an exothermic property by a power supply, but it can be preferably selected from the group consisting of indium tin oxide (ITO), a conductive polymer, carbon nanotubes (CNT), graphene, transparent metal oxide (TCO), and the oxide-metal-oxide multilayer transparent element. Indium tin oxide (ITO) is mixed with Iridium oxide ($In_2O_3$) and tin oxide ($SnO_2$), is typically composed of 90% indium oxide and 10% tin oxide, and is generally referred to as a transparent electrode or ITO. Indium tin oxide, if embodied as a thin film (a thin layer), has the electrical conductivity, is transparent and has no color, and if it is embodied as a lump, it turns to yellow-grey color. Indium tin oxide is deposited on the surface of other materials by an electron beam deposition, vapor deposition, sputtering techniques. Indium tin oxide has been conventionally used in making transparent conductive coating predominantly for liquid crystal displays, flat panel displays, plasma displays, touch screens, electronic paper, organic light emitting diodes, solar cells, antistatic coatings, electronic interference shield. A conductive polymer is called as the plastic that so-called electricity is flowed, and has advantages that the light transmittance is excellent, is lightweight, has superior elasticity and electrical conductivity, and is very easy to process. The conductive polymer is made of the materials of poly acetylene, polyparalenylene, polyphenol, polyaniline and the like, and recently has the case that it is made of polystyrene sulfonic acid and/or PEDOT (poly(3,4-ethylenedioxythiophene)). Carbon NanoTube (CNT) refers to a fine molecule having a diameter of 1 nanometer size wherein carbons connected to the hexagonal ring forms a long tube shape. It is known to have a tensile strength stronger than steel, excellent flexibility, light weight, and very high electrical conductivity. On the other hand, when the purified Single-Walled Carbon Nanotube (SWNT) is dispersed in a solvent with a surfactant and fabricated by using a vacuum filter apparatus, the transparent conductor having all transparence and conductivity is formed. Graphene is a material isolated from graphite in early 2000s, and is nanomaterial composed of carbons whose atomic number is No. 6, such as carbon nanotubes and Fullerene. Graphene has been known to have 100 times or more of electrical conductivity over that of copper, and the excellent elastic force, and is recently embodied as a transparent electrode and is used in various applications. Transparent Metal Oxide (TCO) is collectively referred to as the material having a transparency among the various metal oxides combined with oxygen, and includes ZnO, $SnO_2$, $TiO_2$, etc. Transparent metal oxide has a high conductivity and transparency, and can be used as a coating material at low cost. An oxide-metal-oxide multilayer transparent element is manufactured by a roll-to-roll sputtering process, and may be embodied to have flexibility and low resistance of metal, and high transmittance of the oxide, and includes ITO-Ag (or Cu)-ITO, AZO-Ag-AZO, GZO-Ag-GZO, IZO-Ag-IZO, IZTO-Ag-IZTO and the like. On the other hand, according to FIGS. 14-15, the heat block (200) can be embodied as the various shapes, but is preferably embodied as the flat plate shape. Since the heat block (200) in the flat plate shape has a broad surface area contacting with the micro PCR chip (1), preferably the chip in the flat plate shape, it can evenly provide the heat to the mixture of PCR sample and reagents, and thus can rapidly carry out the change of the temperature in each cycle of the PCR step. On the other hand, in order to accurately monitor the real-time PCR products, it is necessary to increase the sensitivity of the optical signal as far as possible. Since the heat block (200) can be embodied to overall have optical transparency, it can directly transmit the excitation light emitted from the light source to increase the sensitivity of the optical signal. However, some of the excited light can be acted as noise by being reflected on the heat block (200), or being reflected after passing through the heat block (200). Thus, preferably, the sensitivity of the optical signal can be increased by processing the bottom surface of the heat block (200) with the light-absorbing substance. The light absorbing material can be mica, for example, is not limited as long as it is a substance having a property of absorbing the light. Thus, the light absorbing layer can absorb a portion of light derived from a light source to minimize the occurrence of reflected light which acts as a noise of the optical signal. Further, alternatively, it is possible to increase the sensitivity of the optical signal by processing the material preventing the light reflection on the upper surface of the heat block (200). The materials preventing the light reflection can be fluorides such as $MgF_2$, oxide such as $SiO_2$, $Al_2O_3$, but are not limited as long as it is a substance having a property capable of preventing reflection of light. More preferably, the sensitivity of the optical signal can be increased by processing the light-absorbing material at the bottom surface of the heat block (200), and simultaneously by processing the material preventing the light reflection on the upper surface of the heat block (200). That is, in order to monitor the effective real-time PCR, the ratio of the optical signal to the noise should have a maximum value as far as possible, and the ratio of the optical signal to the noise can be improved as long as the reflectance of the emitted light from the PCR chip is lower. For example, the reflectance of the emitted light of the existing heat blocks made of general metallic materials is about 20% to 80%, but when using the heat block (200) comprising said layer absorbing light or the layer reflecting light, the light reflectance can be reduced within from 0.2% to 4%, and when using the heat block (200) comprising the layer absorbing the light (60) and the layer preventing the light reflection (70), the light reflectance can be reduced to 0.2% or less.

The light-detecting module (300) can include a light-providing unit which is disposed to provide the light to the micro PCR chip (1) (not shown) and a light-detecting unit which is drivably disposed to receive light emitted from the micro PCR chip (1) (not shown). The light-providing unit is a module for providing the light to the micro PCR chip (1), and the light-detecting unit is a module for receiving the light emitted from the micro PCR chip (1) to measure the PCR product proceeded in the micro PCR chip (1). Light is emitted from the light-providing unit, the emitted light is passed through or reflected from the micro PCR chip (1), specifically the PCR reaction chamber within the unit module (50) of the micro PCR chip (1), and in this case, the optical signal generated by the nucleic acid amplification within the PCR reaction chamber can be detected by the light-detecting unit. Therefore, according to the real-time PCR apparatus (1000) according to another embodiment of the present invention, it can be determined and analyzed as to whether the amplification of the target nucleic acid contained in the initial PCR sample and reagents is made and as to the degree of amplification, by monitoring the nucleic acid amplification product (to which fluorescent substance is bound) in real time in the PCR reaction chamber during the proceeding of the PCR procedure. Moreover, the light-providing unit and light-detecting unit can be all disposed above and below based on the heat block (200), or can be disposed, respectively. Provided that, the arrangement of the light-providing unit and the light-detecting unit is varied under the consideration of the arrangement relation with other modules for the optimum embodiment of the real-time PCR apparatus (1000) according to another embodiment of the present invention, and preferably, the light-providing unit and light-detecting unit (light-detecting module, 300) are all disposed on the upper of the heat block (200).

The light-providing unit includes the first optical filter for selecting light having a predetermined wavelength of light emitted from the light source, and first light lens for collecting the light emitted from the first optical filter, and may further include a first aspheric lens disposed to spread the light between said light source and said first optical filter. The light source includes all light sources capable of emitting light, and includes an LED (Light Emitting Diode) light source and a laser light source. The first optical filter is one selecting the light having a particular wavelength of the incident lights having different wavelength bands and releasing it, and can be variously selected according to the pre-determined light sources. For example, the first light filter can only pass light of a wavelength band of 500 nm or less among the light emitted from the light source. The first optical lens is one that plays a role to collect the incident light and to increase the intensity of the emitted light, and can increase the intensity of the light irradiated on the micro PCR chip (1) via the heat block (200). Also, the light-providing unit may further include the first aspheric lens disposed to spread the light between the light source and the first light filter. By adjusting the direction of the arrangement of the first aspherical lens, the range of the light emitted from the light source is enlarged to reach a measurable region. The light-detecting unit includes the second optical lens collecting the light emitted from the micro PCR chip (1), the second optical filter selecting the light having the predetermined wavelength among the lights emitted from the second light lens 2, and an optical analyzer detecting an optical signal from the light emitted from said second optical filter, and further includes the second aspherical lens disposed to integrate the light emitted from the second light filter between the second light filter and the optical analyzing device, and may further include a photodiode integrated circuit (PDIC) which is disposed to remove a noise emitted from the second aspherical lens between the second aspherical lens and the optical analyzer and to amplify the light emitted from the second aspheric lens. The second optical lens possesses the role of collecting the incident light and to increase the intensity of the emitted light, and facilitates the detection of the optical signal by increasing the intensity of light emitted from the micro PCR chip (1) via a heat block (200). The second optical filter is one selecting the light of a particular wavelength of incident light having a different wavelength band and releasing it, and can be selected in various ways depending on the wavelength of the predetermined light emitted from the micro PCR chip (1) via a heat block (200). For example, the second optical filter can pass only the light of a wavelength band of 500 nm or less among the predetermined lights emitted from the micro PCR chip (1) via said heat block (200).

The optical analyzer is a module for detecting an optical signal from the light emitted from the second light filter, and allows qualitative and quantitative measurements by converting the expression fluorescence from the PCR sample and reagents into an electric signal. Further, the light-detecting unit further comprises a second aspherical lens disposed to integrate the light emitted from the second light filter between the optical filter and the optical analyzer. By adjusting the arrangement direction of the second aspherical lens, the region of the light emitted from the second light filter is extended to reach a measurable region. In addition, the light-detecting unit further includes a Photodiode Integrated Circuit (PDIC) which is disposed to remove a noise emitted from the second aspherical lens between the second aspherical lens and the optical analyzer and to amplify the light emitted from the second aspheric lens. By using the Photodiode Integrated Circuit (340), the miniaturization of the apparatus is more possible, and the reliable optical signal can be determined by minimizing the noise. Furthermore, the real-time PCR apparatus (1000) according to another embodiment of the present invention can further include one or more dichroic filter for controlling the proceeding direction of the light emitted from the light-providing unit to reach the light-detecting unit, and for isolating the light having the pre-determined wavelength. The dichroic filter is a module selectively transmitting the light according to the wavelength or reflecting the light in the selectively adjusted angle. The dichroic filter is disposed to incline at an angle of about 45 degrees to the axis of light emitted from the light-providing unit, and allows the light to reach the micro PCR chip (1) disposed on the heat block (200) by selectively transmitting a short-wavelength component according to its wavelength and reflecting the long-wavelength component rectangularly. Also, the dichroic filter is disposed to incline at an angle of about 45 degree to the axis of light emitted from the light-providing unit, and allow the light to reach the light-detecting unit by selectively transmitting a short-wavelength component according to its wavelength and reflecting the long-wavelength component rectangularly. The light arrived to the light-detecting unit is converted into the electric signal in the light detector to display as to whether the nucleic acid is amplified and the amplification degree.

Figure 16:
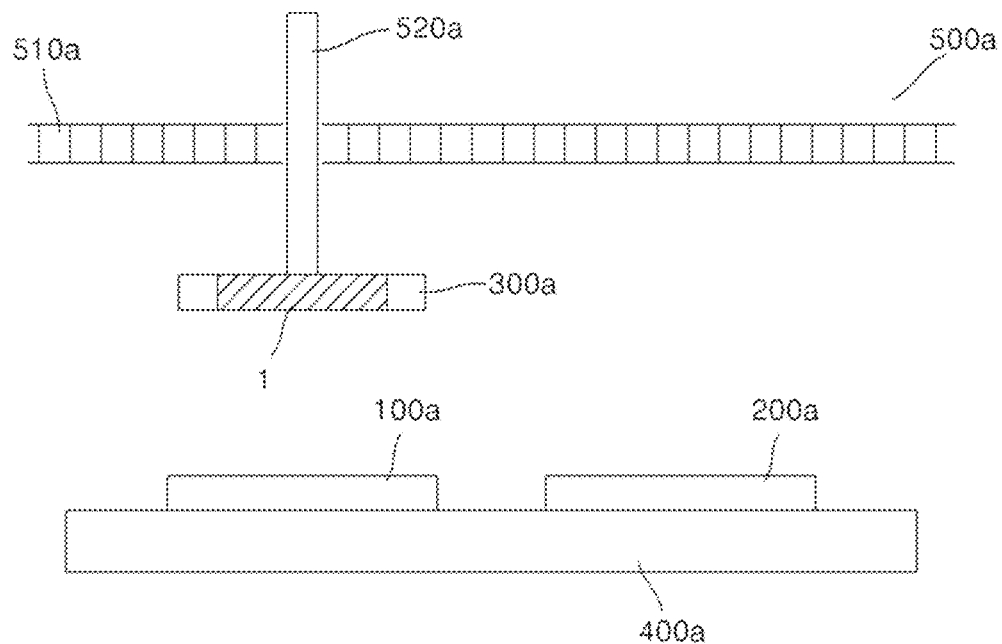
FIGS. 16-18 relate to a real time PCR apparatus according to another embodiment of the present invention, which comprises a micro PCR chip according to an embodiment of the present invention, two heat blocks, the chip holder that the micro PCR chips are movable between the two heat blocks by the driving means, being equipped with the micro PCR chip, and a light-detecting module which is implemented to detect a optical signal generated from the micro PCR amplification of PCR reaction chamber inside the micro PCR chips during the movement between the two heat blocks by the driving means.
Figure 17:
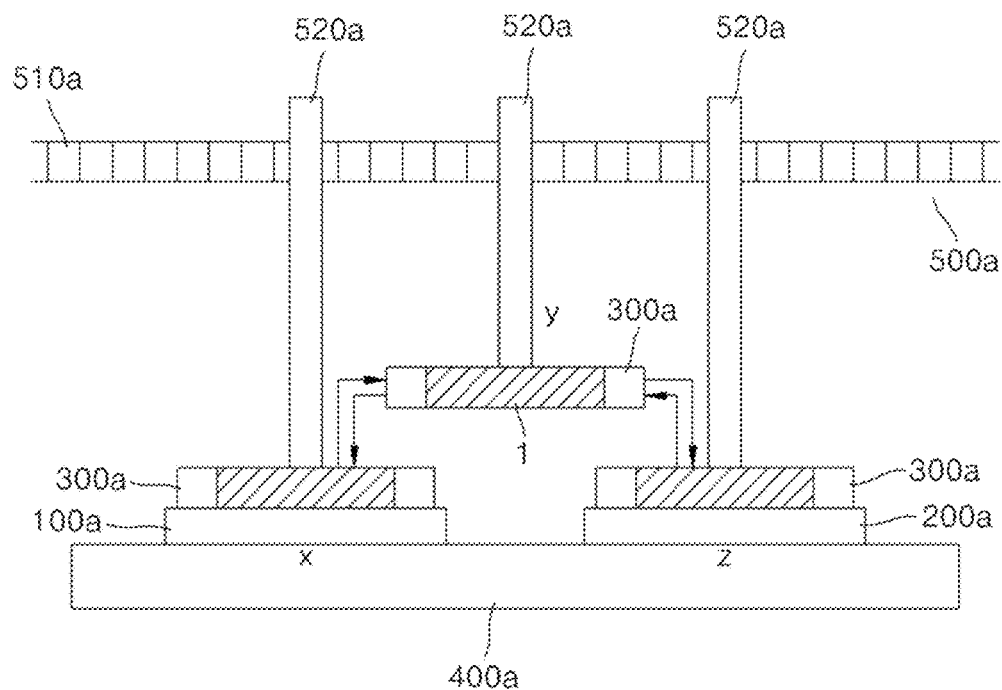
Figure 18:
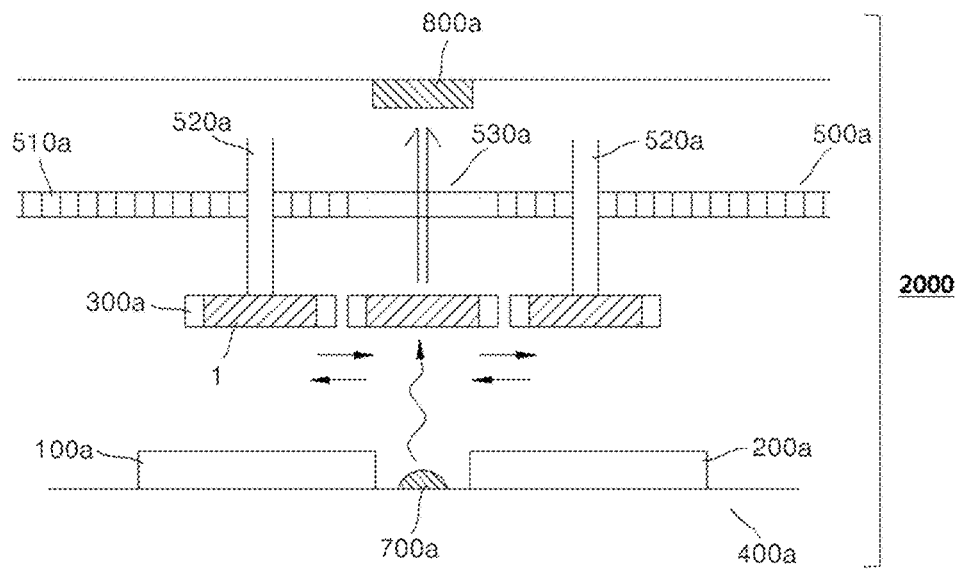

FIGS. 16-18 display the real-time PCR apparatus equipped with two heat blocks to which micro PCR chip according to an embodiment of the present invention is applied.

According to FIGS. 16 to 18, the real-time PCR apparatus (2000) according to another embodiment of the present invention comprises a micro PCR chip (1) according to one embodiment of the present invention described above; the first heat block (100a) disposed on a substrate (400a) but is embodied to heat contact with the micro PCR chip (1); the second heat block (200a) which is spaced apart from the first heat block (100a) on the substrate (400a) but is embodied to heat-contact with the micro PCR chip (1); a chip holder (300a) which is able to move left and right and/or above and below, and with which the micro PCR chip (1) is equipped; and a light-detecting module (700a, 800a) which is disposed between the first heat block (100a) and the second heat block (200a), but is embodied to detect the optical signal generated from the PCR amplification product in an interior of the PCR reaction chamber (10) of the micro PCR chip (1) when moving the micro PCR chip (1) is moved between the first heat block (100a) and the second heat block (200a) by the driving means (500a).

According to FIG. 16, the real-time PCR apparatus (2000) according to another embodiment of the present invention comprises the first heat block (100a) disposed on the substrate (400a); the second heat block (200a) disposed apart to the first heat block (100a) on the substrate (400a); and the chip holder (300a) which is able to move left and right and/or above and below, and with which the micro PCR chip (1) according to one example of the present invention is equipped.

The substrate (400a) includes all materials that do not change in their physical and/or chemical properties due to the heating of the first heat block (100a) and the second heat block (200a) and the maintaining of the temperature, and have a material which does not allow heat exchange with each other between the first heat block (100a) and the second heat block (200a). For example, the substrate (400a) comprises the material, such as plastic, etc or may be composed of such materials.

The first heat block (100a) and the second heat block (200a) are to maintain the temperature for carrying out the denaturation step for amplifying nucleic acids, annealing step and extension (or amplification) step. Therefore, the first heat block (100a) and the second heat block (200a) include various modules for providing the necessary temperature required for the respective stages, and maintaining it, or can be drivingly connected with such modules. Therefore, when the chip holder (300a) equipped with the micro PCR chip (1) is in contact with one surface of the respective heat block (100a, 200a), since the first heat block (100a) and the second heat block (200a) can overall heat the contact surface with the micro PCR chip (1) and maintain the temperature, they can uniformly heat the sample solution in the micro PCR chip (1) and maintain the temperature. In conventional PCR devices using a single heat block, the rate for the temperature change in the single heat block is performed in the range of 3 to 7° C. per second, but in the real-time PCR device (2000) comprising two heat blocks according to another example of the present invention, since the rate of temperature change at each heat block (100a, 200a) is made in the range of 20 to 40° C. per second, PCR proceeding time can be greatly shorten.

The first heat block (100a) and the second heat block (200a) comprise a heat wire (not shown) which is disposed therein. The heat wire can be drivably connected to various heat sources so as to maintain the temperature for performing the steps of the denaturing step, annealing step and extension (or amplification) steps, and can be drivably connected to various temperature sensors for monitoring the temperature of the hot wire. Said heat wire can be disposed to be symmetrical in up and down and/or left and right direction based on the center point of the plane of the respective heat block (100a, 200a) so as to overall and constantly maintain the internal temperature of the first heat block (100a) and the second heat block (200a). The arrangement of the heat wires in up and down and/or left and right symmetrical direction can be various. In addition, the first heat block (100a) and the second heat block (200a) comprise the thin film heater (not shown) which is disposed therein. The thin film heater can be disposed spacing apart up and down and/or left and right direction based on the central point of the plane of each heat block (100a, 200a) so as to overall and constantly maintain the internal temperature of the first heat block (100a) and the second heat block (200a). The arrangement of the thin film constantly spacing apart up and down and/or left and right direction can be various.

The first heat block (100a) and the second heat block (200a) can comprise a metal material, for example aluminum material or be composed of aluminum material for the uniform heat distribution and rapid heat transfer on the same area.

The first heat block (100a) can be embodied to maintain the proper temperature for performing the denaturation step or annealing, and extending (or amplification) step. For example, the first heat block (100a) of the real-time PCR apparatus (2000) according to another example of the present invention can maintain 50° C. to 100° C., and when performing the denaturation step, it can maintain 90° C. to 100° C., preferably, it can maintain 95° C. to 100° C., and when performing the annealing and extending (or amplification) steps, it can maintain 55° C. to 75° C., and preferably 75° C. Provided that, if the above-mentioned denaturation step, or annealing and extending (or amplification) steps can be performed, the temperature is not limited thereto. The second heat block (200a) can be embodied to maintain the proper temperature for performing the denaturation step, or annealing and extending (or amplification) steps. For example, the second heat block (200a) of the PCR apparatus according to the third example of the present invention, when performing the denaturation step in the second heat block (200a), can maintain 90° C. to 100° C., and preferably can maintain 95° C., and when performing the annealing and extending (or amplification) steps, it can maintain 55° C. to 75° C., and preferably 75° C. Provided that, if the above-mentioned denaturation step, or annealing and extending (or amplification) steps can be performed, the temperature is not limited thereto. Therefore, the first heat block (100a) can maintain the denaturing temperature of PCR, if the denaturing temperature is lower than 90° C., the denaturation of nucleic acid which becomes a template of PCR is occurred and an efficiency is lower and thus PCR efficacy is fallen or the reaction does not occurred, if the temperature of the denaturation step is higher than 100° C., the enzyme utilized in PCR loses its activity, and thus the temperature of the denaturation step can be a 90° C. to 100° C., and preferably can be 95° C. In addition, the second heat block (200a) can maintain the temperature of annealing and extension (or amplification) steps. If the temperature of extension (or annealing) step is lower than 55° C., the specificity of PCR product may be lower, and if the temperature of annealing and extension (or amplification) steps is higher than 74° C., since the extension by the primer may not be occurred, the efficacy of PCR is lower, and thus, the temperature of annealing and extension (or amplification) steps may be 55° C. to 75° C., and preferably 72° C.

The first heat block (100a) and the second heat block (200a) are disposed spacing apart at the pre-determined distance not to occur the mutual heat exchange. Thus, since the heat exchange between the first heat block (100a) and the second row of block (200a) does not occur, it is possible to control the accurate temperature control between the denaturing step and the annealing and extension (or amplification) steps in the nucleic acid amplification reaction that can undergo even significant impact by a fine temperature variation.

Real-time PCR apparatus (2000) according to another example of the present invention comprises a chip holder (300a) which can be moved left and right and/or up and down by the driving means (500a) on the first heat block (100a) and the second heat block (200a) and that the micro PCR chip (1) is equipped. The chip holder (300a) is a module wherein the real time PCR apparatus (2000) is equipped with the micro PCR chip (1). Inner wall of the chip holder (300a), when the nucleic acid amplification reaction is carried out by the real time PCR apparatus (2000), has a shape or structure for fix-disposing to the outer wall of the micro PCR chip (1) not to be separated from the tip holder (300a). The chip holder (300a) is connected so as to drive to the driving means (500a). Further, the micro PCR chip (1) is detachably attached to the chip holder (300a).

The driving means (500a) comprise all the means that allow the chip holder (300a) equipped with the micro PCR chip (1) to move left and right and/or up and down on the first heat block (100a) and the second heat block (200a). By movement of the driving means (500a) in left and right directions, the chip holder (300a) equipped with the micro PCR chip (1) can reciprocally move between said first heat block (100a) and the second heat block (200a), and by the movement of the driving means (500a) in up and down direction, the chip holder (300a) equipped with the PCR chip (10) can be attached to or separated from the first heat block (100a) and the second heat block (200a). The driving means (500a) of the real-time PCR apparatus (2000) shown in FIG. 16 comprises a rail (510a) extending in the left and right direction, and a connecting member (520a) which is disposed to be movable in left and right directions by sliding mode via the rail (510a) and is movable in up and down direction by sliding mode, and one end of the connecting member (520a) is equipped with the chip holder. The movement of the driving means (500a) in left and right and/or up and down direction can be controlled by a control means (not shown) which is drivably disposed at the internal or external of the PCR apparatus, and the control means can control an attachment and a separation between the chip holder (300a) equipped with the micro PCR chip (1) for the denaturation step of PCR and the annealing and extension (or amplification) step and the first heat block (100a) and the second block (200a).

FIG. 17 illustrates each stage of the nucleic acid amplification reaction by the movement of the chip holder of the real-time PCR apparatus (2000) according to another example of the present invention. The nucleic acid amplification reaction by the real-time PCR apparatus is performed by the following steps.

First, the step is performed, wherein the micro PCR chip (1) is introduced with the sample solution comprising nucleic acid, for example, a double-stranded DNA, oligonucleotide primer having the specific base sequence and complementary sequence to be amplified, DNA polymerase, trioxide deoxyribonucleotide (dNTP) and PCR buffer, and the PCR chip (10) is disposed on the chip holder (300a). After that, or at the same time, the first heat block (100a) is heated and maintained at the temperature for the denaturation step, for example, 90° C. to 100° C., and preferably is heated and maintained at 95° C. The step is performed wherein the second heat block (200) is heated to and maintained at the temperature for the annealing and extension (or amplification) steps, for example, at 55° C. to 75° C., and preferably heated to and maintained at 72° C. Then the first denaturation step is performed by controlling the connecting member (520a) of the driving means (500a) to move the micro PCR chip (1) downwards, and the chip holder (300a) equipped with the micro PCR chip (1) is attached to the first heat block (100a) to perform the first denaturation step of PCT (x step). Then, the first denaturation step of PCR is completed by controlling the connecting member (520a) of the driving means (500a) to move the micro PCR chip (1) upwards, by separating the chip holder (300a) equipped with the micro PCR chip (1) from the first heat block (100a) to complete the first denaturation step of PCR, and the step for moving the micro PCR chip (1) on the second heat block (200a) by controlling the connecting member (520a) of the driving means (500a) (y step). Then, the first annealing and extension (or amplification) steps of PCR are performed by controlling the connecting member (520a) of the driving mean (500a) to move the micro PCR chip (1) downwards, and by contacting the chip holder (300a) equipped with the micro PCR chip (1) to the second heat block (100a) (z step). Finally, the first annealing and extension (or amplification) steps are completed by controlling the connecting member (520a) of the driving means (500a) to move the micro PCR chip (1) upward, and by separating the chip holder (300a) equipped with the micro PCR chip (1) from the second heat block (100a), and the nucleic acid amplification reaction is performed by controlling the connecting member (520a) of the driving means (500a) to move the micro PCR chip (1) on the first heat block (100a), and by repeating the above x, y and steps (circulation step).

FIG. 18 shows the step for observing the nucleic acid amplification reaction in real time by using the real-time PCR apparatus (2000) according to another example of the present invention. The above real-time PCR apparatus (2000) comprises the light-detecting module (700a, 800a) which is disposed between the second heat blocks (200a), but is embodied to detect the optical signal generated from the PCR amplification product in the interior of PCR reaction chamber (10) of the micro PCR chip (1), when the micro PCR chip (1) is moved between the first heat block (100a) and the second heat block (200a) by the driving means (500a), specifically, a light source (700a) and a light-detecting portion (800a). That is, the real-time PCR apparatus (2000) is equipped with the light source (700a) between the first heat block (100a) and the second heat blocks (200a), is equipped with the light-detecting portion (800a) for detecting the light emitted from the light source (700a) on the chip holder (300a), or is equipped with the light-detecting portion (800a) for detecting the light emitted from the light source (700a) between the first heat block (100a) and the second heat block (200a), and is equipped with the light source (700a) on the chip holder (300a). Further, the light-detecting unit (800a) is disposed on an upper of the driving means (500a), the driving means (900a) is equipped with a through portion (530a) for passing the light emitted from the light source (700a).

By the arrangement of the light source (700a) and the light-detecting unit (800a), the extent to which the nucleic acid is amplified in the micro PCR chip (1) in the nucleic acid amplification reaction by the real-time PCR apparatus (2000) can be detected in real time. In order to detect the extent to which the nucleic acid is amplified by the micro PCR chip (1), an additional fluorescent material can be added to the sample solution introduced into the micro PCR chip (1). The light source (700a) is disposed so as to be distributed as broad as possible in the spaced space between the first heat block (100a) and the second heat block (200a), and is disposed to emit the light as same as possible. The light source (700a) can be drivably connected and disposed to a lens (not shown) collecting the light emitted from the light source (700a), and an optical filter (not shown) for filtering light of a particular wavelength band.

Steps for detecting the extent to which the nucleic acid is amplified in the micro PCR chip (1) at the time of the nucleic acid amplification by the real time PCR apparatus (2000) are as follows.

When the micro PCR chip (1) is moved from the upper of the first heat block (100a) to the upper of the second block (200a) by controlling the connecting member (520a) of the driving means (500a) after completing the first denaturation step of the PCR, or the micro PCR chip (1) is moved from the upper of the second heat block (200a) to the upper of the first heat block (200a) by controlling the connecting member (520) of the driving means (500a) after completing the first annealing and extension (or amplification) steps of the PCR, a step for stopping the chip holder (300a) equipped with the micro PCR chip (1) on the spaced space between the first heat block (100a) and the second heat block (200a) by the connecting member (520) of the driving means (500a) is performed. Thereafter, the light is emitted from the light source (700a), the emitted light is passed the micro PCR chip (1), specifically, the PCR reaction chamber of the micro PCR chip (1), and in this case, the light-detecting portion (800a) detects the optical signal generated by amplification of a nucleic acid in the PCR reaction chamber. In this case, the light passed through the micro PCR chip (1) with the light-transmitting material is passed the driving means (500a), specifically the passing through portion (530a) disposed in the rail (510a) to reach the passing through portion (800a). Therefore, by monitoring the reaction result by the amplification of the nucleic acid (fluorescent material is bonded) in real time during proceeding each cycle stage of the PCR, the amount of the target nucleic acids included in the first reaction sample can be determined and analyzed in real time.

Example 1. Preparation of Micro-PCR Chip

Figure 19:
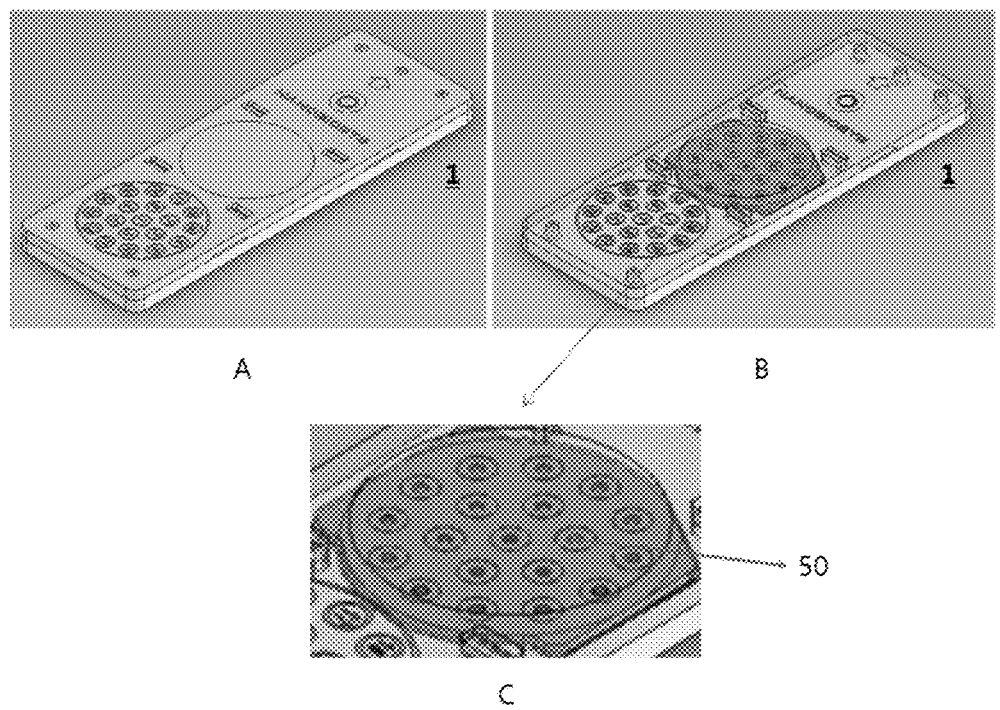
FIG. 19 is a practical implementation view of the micro PCR chip according to an embodiment of the present invention.

As shown in FIG. 12, the first to third plates (100, 200, 300) of plastic material in the flat shape were prepared. The first plate (100) was prepared with a thickness of 0.5 mm, the second plate (200) was prepared with a thickness of 2 mm, but by integrating nineteen PCR reaction chambers (10) in a central circular region, and the third plate (300) was prepared with a thickness of 2 mm, but by forming the light transmission portion (25) to embody a circular groove corresponding to the central circular region on its lower end surface and to protrude toward to the interior of nineteen the PCR reaction chambers. In addition, a flexible packing portion (50) which can be coupled in correspondence with the circular groove of the third plate (300) and the light transmission portion (50) was prepared and attached to a lower end surface of the third plate (300). Then, a double-sided adhesive tape was bonded to the upper of the first plate (100) and the second plate (200) was attached to the upper of the first plate (100). In this case, the first plate (100) and second plate (200) can be of course attached to each other via a thermal conjugation in addition to the double-sided adhesive tape, an ultrasonic conjugation, a UV conjugation, a solvent conjugation method, etc. Thereafter, the PCR reaction chamber (10) was sealed by injecting the PCR sample and reagents to nineteen PCR reaction chambers (10) formed by the attachment of the second edition (200), and by attaching the third plate (300) attached by the flexible packing part (50) to the upper of the second plate (200). According to FIG. 19, it was possible to confirm the completed micro PCR chip (1) in this example. Diagram A of FIG. 19 is an external view of the micro PCR chip according to one example of the present invention, diagram B is the external view reflecting a perspective view of a third plate (300) in the micro PCR chip (1) of diagram A, and diagram C is an enlarged view showing a state in which nineteen unit modules (50) are disposed in a circular region of the micro PCR chip (1) of diagram B.

Example 2. Preparation and Synthesis of Primer Set for Detecting Food-Borne Bacteria The primer used for real-time detecting four kinds of food-borne bacteria was prepared via Primer 3 by setting the GC % to be 40% to 60%, and the Tm value to be 65 to 75° C., and the prepared primer was synthesized by requesting to Geno Tech company. Forward/Reverse base sequence of the primer sets for specifically detecting four kinds of food-borne bacteria and the corresponding product size (bp) are as shown in Table 1 below.

TABLE 1

| Strain name | Product size (bp) | Sequence |
|---|---|---|
| Salmonella spp. | 127 | (Forward) TGT TGC GGA ACG CGC TTG ATG AGC TTT (SEQ ID NO: 1) (Reverse) CAG GAA ATT TCG CTT CCA GTT GGT CCA G (SEQ ID NO: 2) |
| Listeria monocytogenes | 221 | (Forward) GCG CCA CTA CGG ACG TTT AAC CAA G (SEQ ID NO: 3) (Reverse) ACA ATC GCA TCC GCA AGC ACT GTA G (SEQ ID NO: 4) |
| Staphylococcus aurens | 127 | (Forward) ATT GGT TGA TAC ACC TGA AAC AAA GCA TCC (SEQ ID NO: 5) (Reverse) AAA GCT TCG TTT ACC ATT TTT CCA TCA GCA (SEQ ID NO: 6) |
| Escherichia coli | 136 | (Forward) ATG TGG CCG GGT TCG TTA ATA CGG (SEQ ID NO: 7) (Reverse) GCT GCG ACA CGT TGC AGA GTG GTA (SEQ ID NO: 8) |

Example 3. Performance of PCR (Comparison Experiment)

PCR was performed by using the PCR apparatus of another company and the real-time PCR apparatus according to one example of the present invention, based on primer sets for detecting four kinds of food-borne bacteria according to one example of the present invention. The conventional PCR device of BIO-RAD Company (BIORAD CFX 3600 Connect™ Real-time PCR) was used as the PCR apparatus of other company. When Comparing it with the real-time PCR apparatus according to one example of the present invention, the PCR apparatus of other company uses PCR vessel with tube type, whereas the PCR device according to one example of the present invention uses PCR vessel with chip type, and has the larger working volume of 20 microliters (µl) in the PCR apparatus in contrast to 12 microliters (µl) of the working volume in the PCR device according to one example of the present invention, and has 21 kg (kg) of the heavier equipment weight of PCR apparatus, in contrast to 5.5 kg of the equipment weight of that of the one example of the present invention.

PCR reaction conditions and driving conditions used for the PCR apparatus according to one example of the present invention are as listed in Tables 2 and 3 below, and PCR reaction condition and the driving condition used in the PCR apparatus of other company are as described in Tables 4 and 5 below.

TABLE 2

| No. | Materials | Volume (μl) |
| --- | --- | --- |
| 1 | NBS 2x rt-PCR Master Mix | 6 |
| 2 | 210 μM Primer F/R | 1.2/1.2 |
| 3 | PCR grade water | 2.6 |
| 4 | Template | 1 |
| | Total | 12 |

TABLE 3

| Temperature | Time | Cycle |
| --- | --- | --- |
| 95° C. | 8 sec | 11 |
| 95° C. | 3 sec | 40 |
| 68° C. | 14 sec | |

TABLE 4

| No. | Materials | Volume (μl) |
| --- | --- | --- |
| 1 | THUNDERBIRD SYBR qPCR mix (TOYOBO, code no. QPS201) | 10 |
| 2 | 10 μMPrimer F/R | 2/2 |
| 3 | PCR grade water | 5 |
| 4 | Template | 1 |
| | Total | 20 |

TABLE 5

| Temperature | Time | Cycle |
| --- | --- | --- |
| 95° C. | 30 sec | 1 |
| 95° C. | 5 sec | 40 |
| 68° C. | 30 sec | |

FIGS. 20-35 show the results of PCR products of PCR devices according to one example of the present invention and the device from another company. Specifically, a real-time PCR was proceeded by introducing a primer (IPAH-shigelle) as a negative control (NC) group to the micro PCR chip according to one example of the present invention, and introducing one ($1 \times 10^5$ copies/g) of four kinds of food-borne bacteria to the second of the reaction chamber (2), and introducing all of four kinds of food-borne bacteria (mix sample) to the third of the reaction chamber (3); results of the real-time PCR were monitored by fluorescence measurement relative to cycles (measuring Ct values); and then photos of electrophoresis were taken.

FIGS. 20-23 relate to the detection and specificity of *Salmonella* spp.

Figure 20:
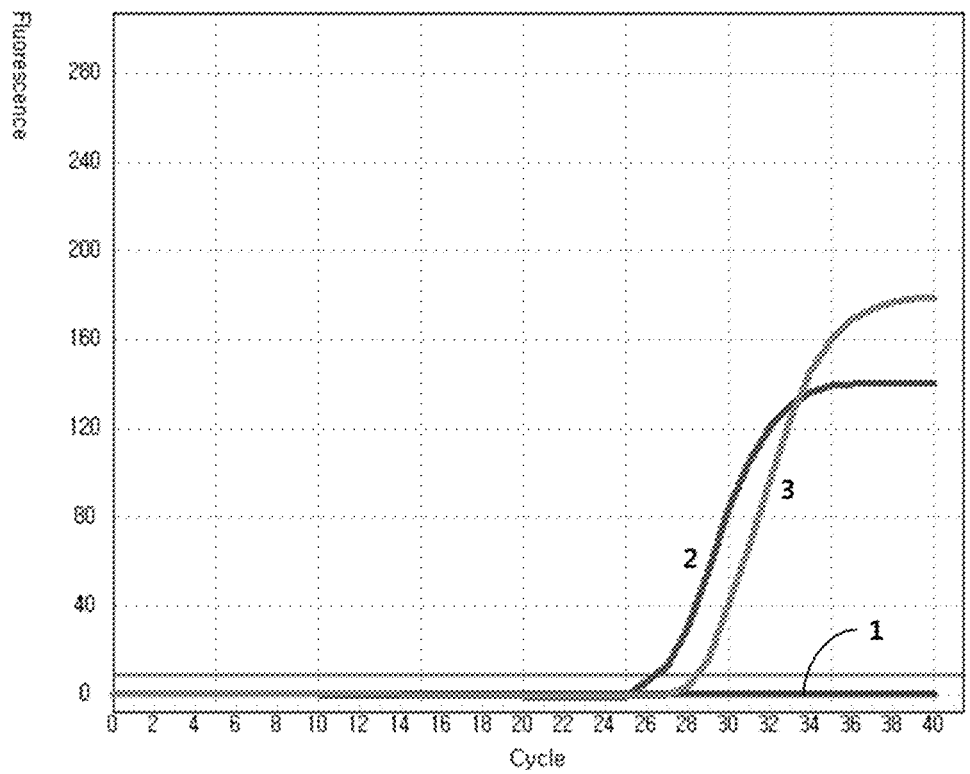
FIGS. 20-35 are materials obtained by confirming the detection result of four food-borne bacteria by comparing and experimenting PCR apparatus according to an embodiment of the present invention and third party PCR device.
Figure 21:
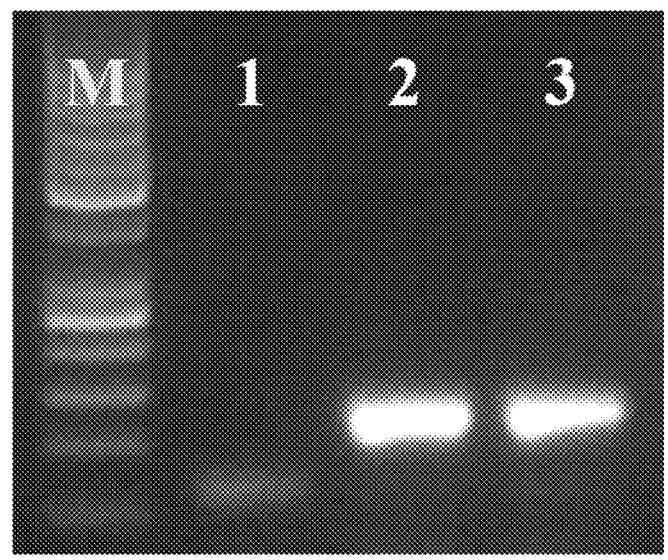
Figure 22:
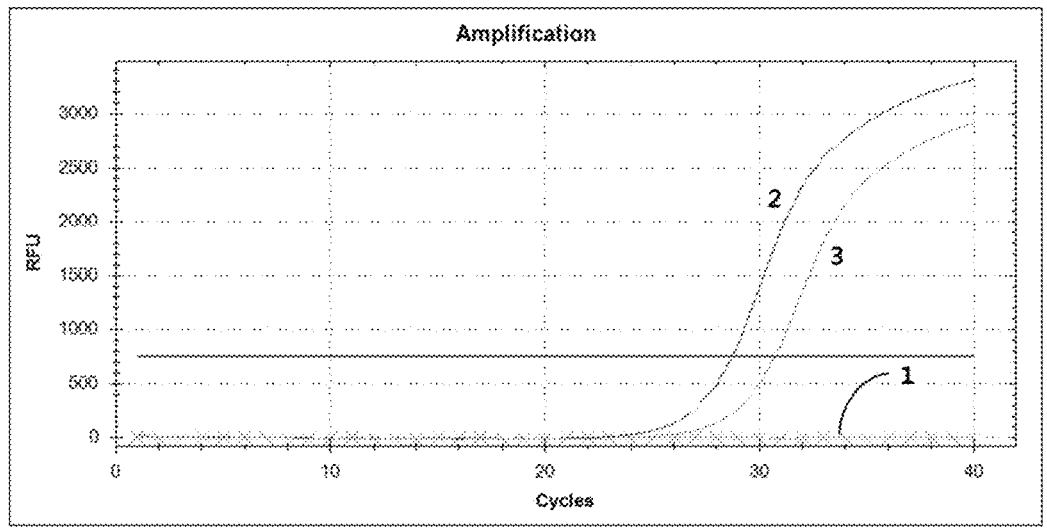
Figure 23:
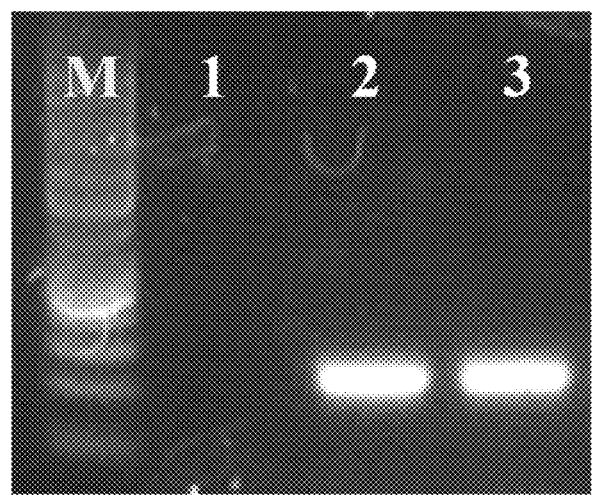

According to FIG. 20, it was identified that as a result the graph of real-time PCR derived by the PCR device according to one example of the present invention, the negative control (NC) of the first reaction chamber (1) has no reaction (Ct value=0), but an effective PCR result was calculated in the second reaction chamber (2) due to the primer sets of SEQ ID NO.: 1 and SEQ ID NO.: 2 (Ct value=22.44), and further the effective PCR result was calculated in the third reaction chamber (3) (Ct value=24.67). Such PCR results can be confirmed again by the electrophoresis photograph of FIG. 21. On the other hand, according to FIG. 22, as the result graphs of real-time PCR produced by the PCR device of other company, it was confirmed again that the negative control (NC) of the first reaction chamber (1) had no reaction (Ct value=0), the effective PCR result was calculated in the second reaction chamber (2) due to the primer sets of SEQ ID NO.: 1 and SEQ ID NO.: 2 (Ct value=28.74), and further the effective PCR result was also calculated in the third reaction chamber (3) (Ct value=30.73). Such PCR results can be confirmed again by electrophoresis photograph of FIG. 23.

FIGS. 24 to 27 relate to the detection and specificity of *Listeria monocytogenes*.

Figure 24:
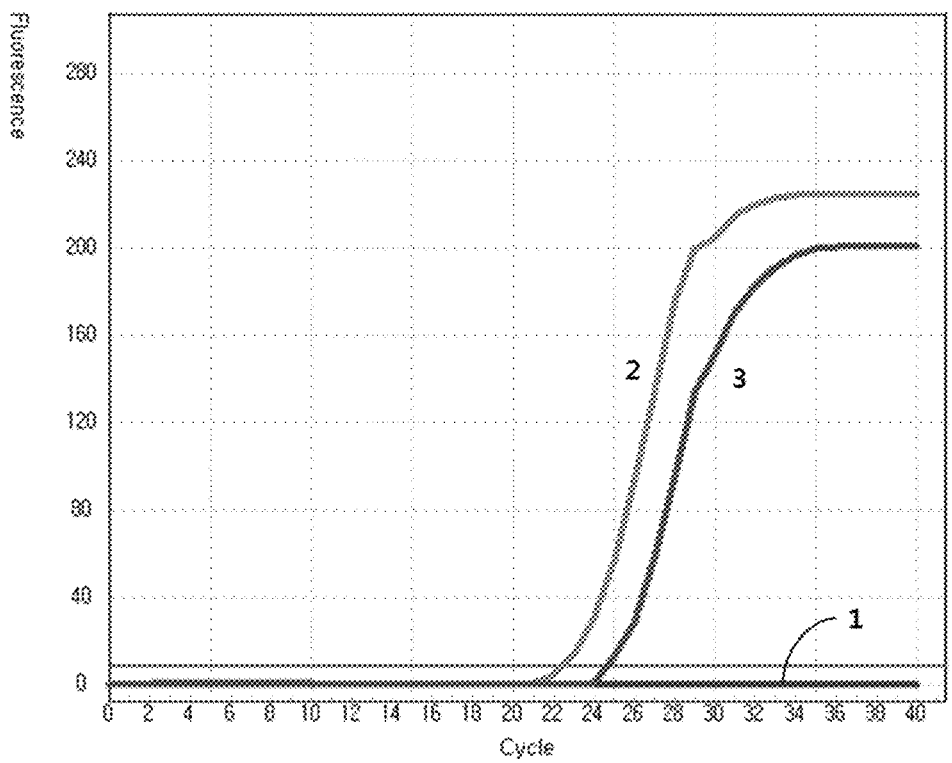
Figure 25:
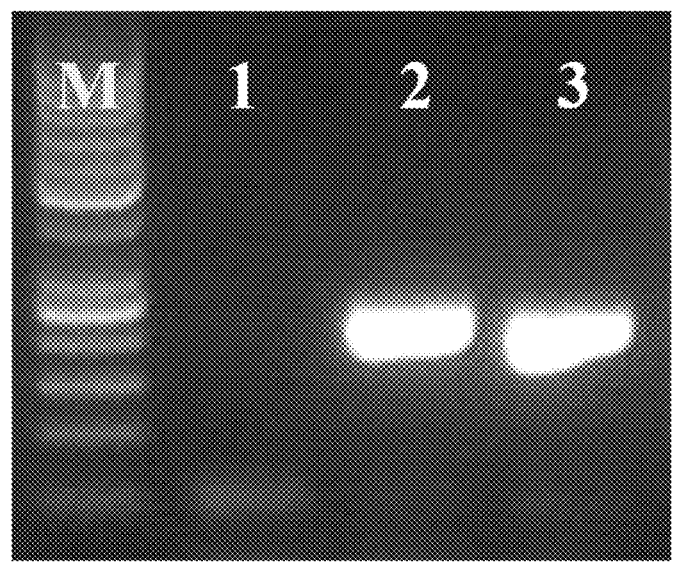
Figure 26:
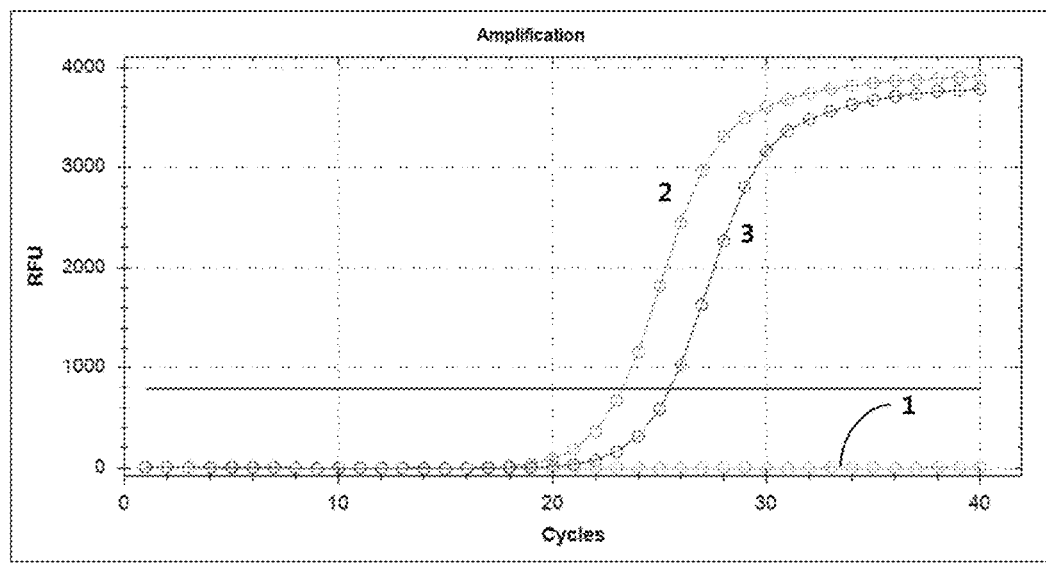
Figure 27:
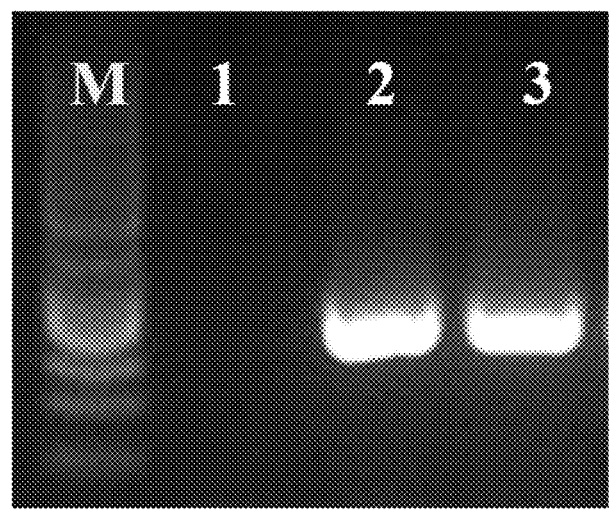
Figure 28:
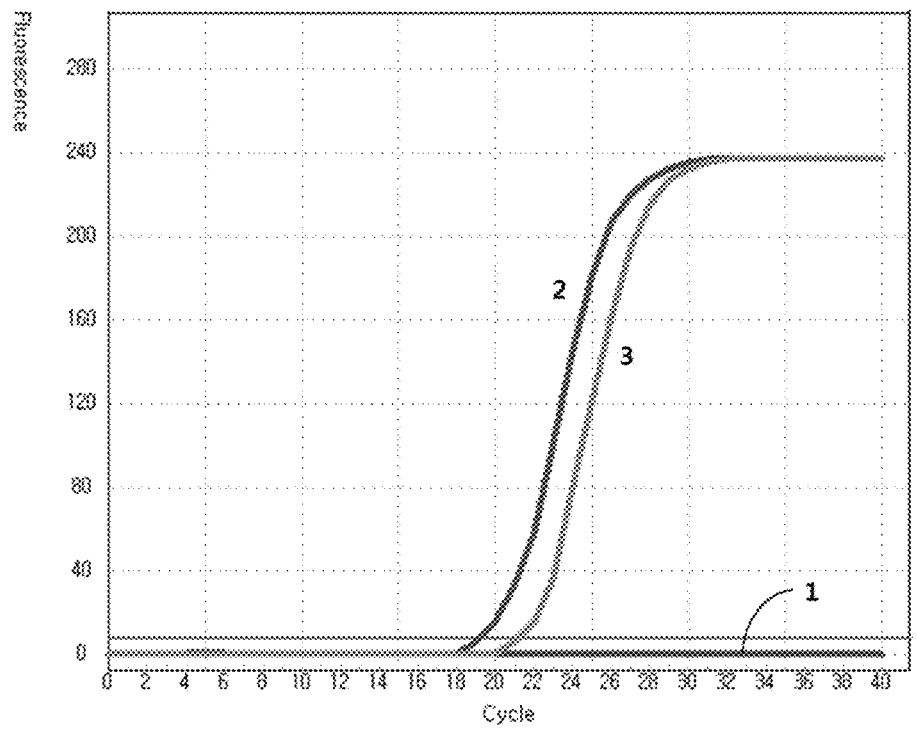
Figure 29:
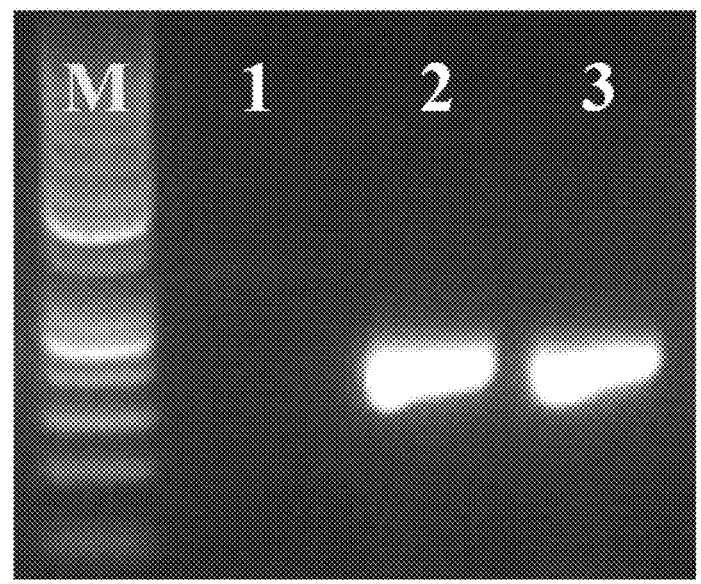
Figure 30:
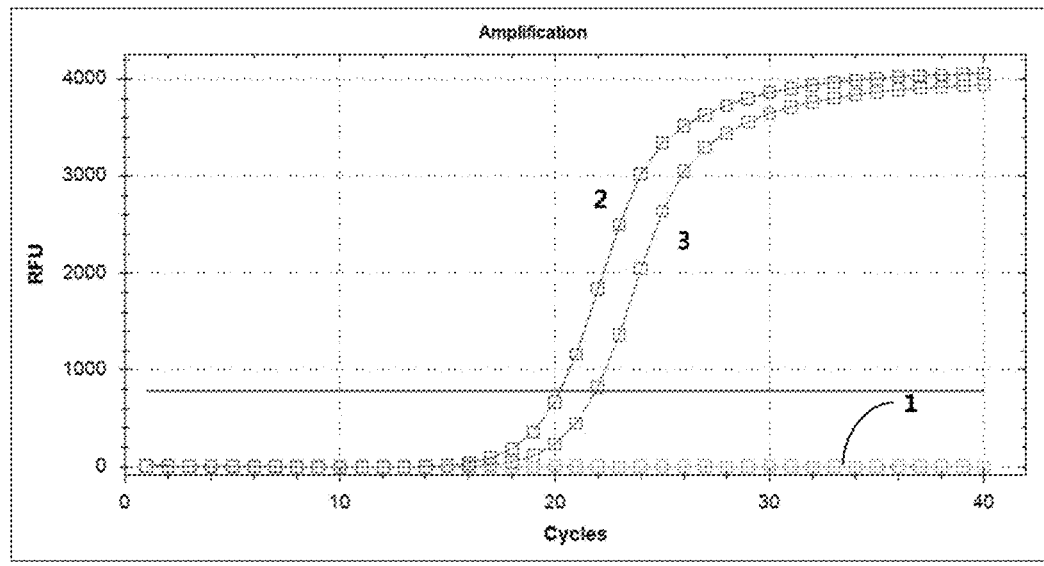
Figure 31:
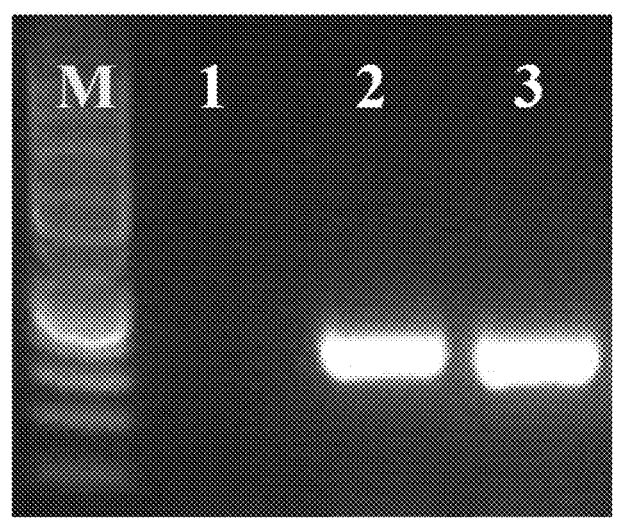

According to FIG. 24, it was identified that as a result graph of real-time PCR derived by the PCR device according to one example of the present invention, the negative control (NC) of the first reaction chamber (1) has no reaction (Ct value=0), but an effective PCR result was calculated in the second reaction chamber (2) due to the primer sets of SEQ ID NO.: 3 and SEQ ID NO.: 4 (Ct value=22.44), and further the effective PCR result was calculated in the third reaction chamber (3) (Ct value=24.67). Such PCR results can be confirmed again by the electrophoresis photograph of FIG. 25. On the other hand, according to FIG. 26, as result graphs of real-time PCR produced by the PCR device of other company, it was confirmed again that the negative control (NC) of the first reaction chamber (1) had no reaction (Ct value=0), the effective PCR result was calculated in the second reaction chamber (2) due to the primer sets of SEQ ID NO.: 3 and SEQ ID NO.: 4 (Ct value=23.23), and further the effective PCR result was calculated in the third reaction chamber (3) (Ct value=25.45). Such PCR results can be confirmed again by electrophoresis photograph of FIG. 27.

FIGS. 28 to 31 relate to the detection and specificity of the *Staphylococcus aurens*. According to FIG. 28, it was identified that as a result graph of real-time PCR derived by the PCR device according to one example of the present invention, the negative control (NC) of the first reaction chamber (1) has no reaction (Ct value=0), but an effective PCR result was calculated in the second reaction chamber (2) due to the primer sets of SEQ ID NO.: 5 and SEQ ID NO.: 6 (Ct value=19.20), and further the effective PCR result was calculated in the third reaction chamber (3) (Ct value=21.22). Such PCR results can be confirmed again by the electrophoresis photograph of FIG. 29. On the other hand, according to FIG. 30, as the result graphs of real-time PCR produced by the PCR device of other company, it was confirmed again that the negative control (NC) of the first reaction chamber (1) had no reaction (Ct value=0), the effective PCR result was calculated in the second reaction chamber (2) due to the primer sets of SEQ ID NO.: 5 and SEQ ID NO.: 6 (Ct value=20.23), and further the effective PCR result was calculated in the third reaction chamber (3) (Ct value=21.91). Such PCR results can be confirmed again by electrophoresis photograph of FIG. 31.

FIGS. 32 to 35 relate to the detection and specificity of the *Escherichia coli*.

Figure 32:
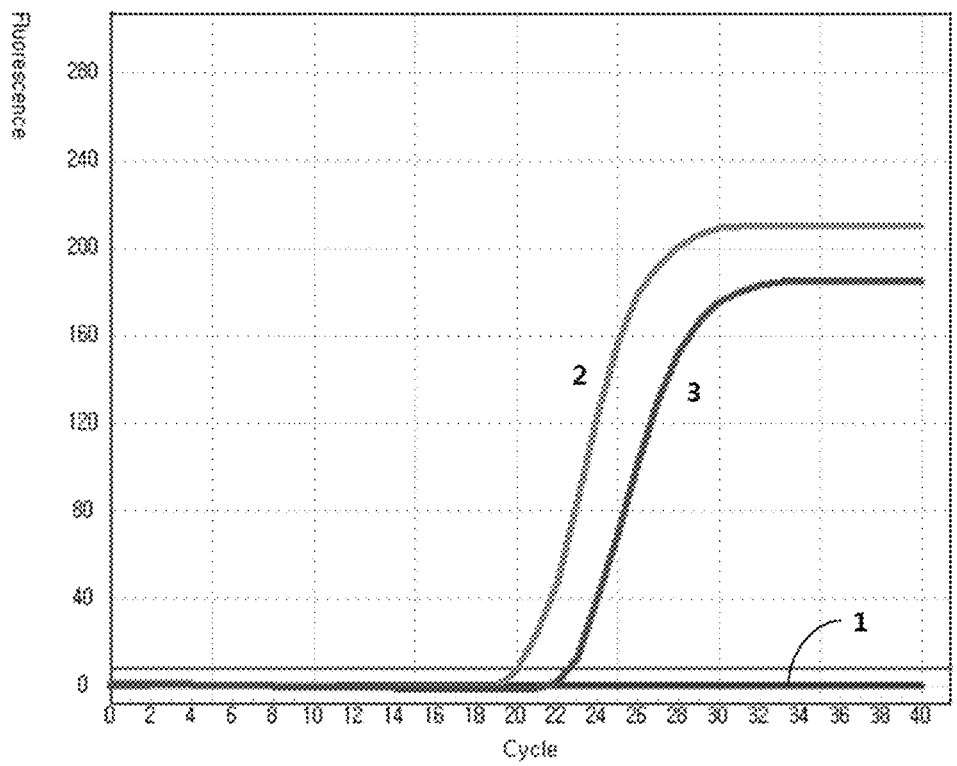
Figure 33:
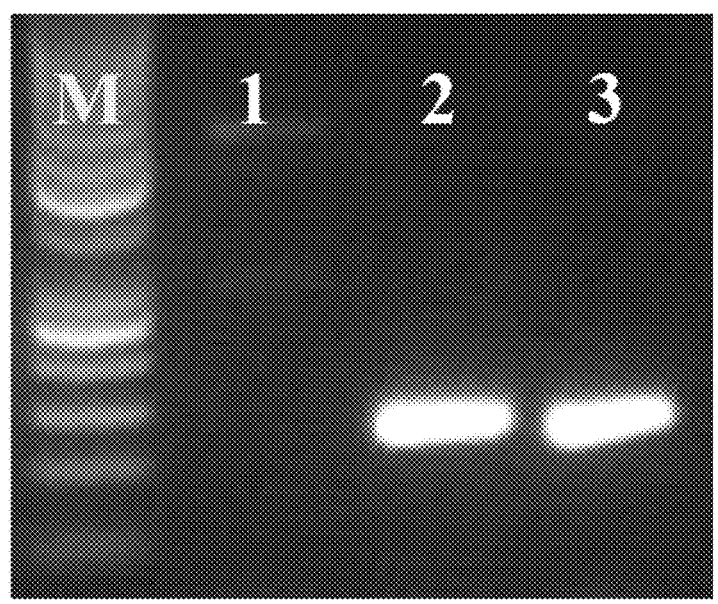
Figure 34:
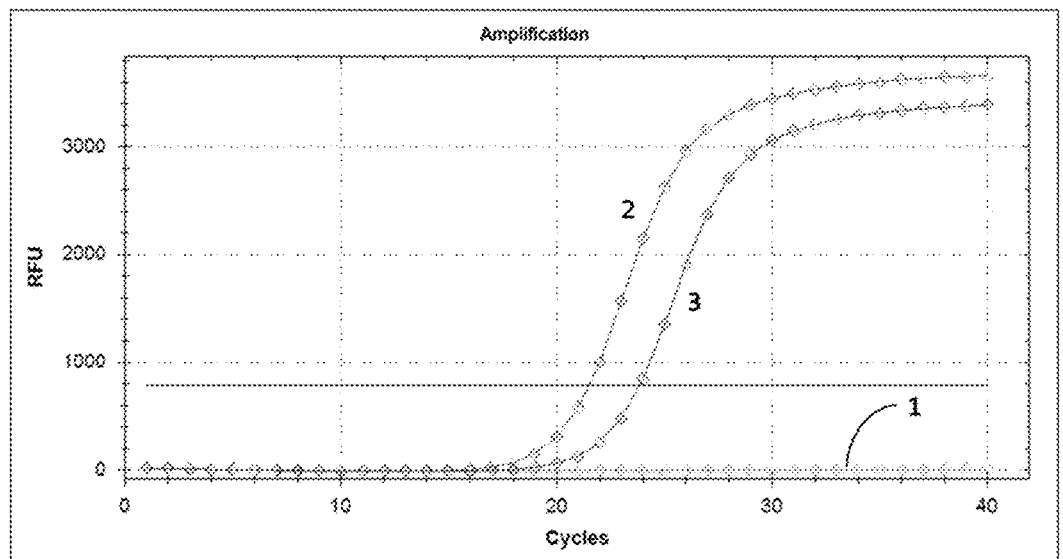
Figure 35:
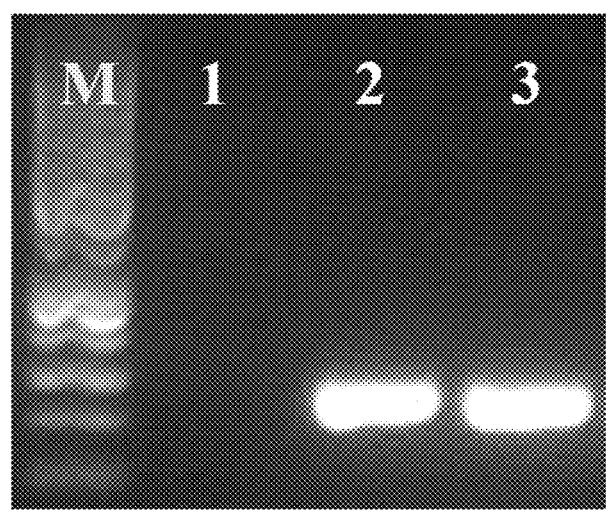

According to FIG. 32, it was identified that as a result graph of real-time PCR derived by the PCR device according to one example of the present invention, the negative control (NC) of the first reaction chamber (1) has no reaction (Ct value=0), but an effective PCR result was calculated in the second reaction chamber (2) due to the primer sets of SEQ ID NO.: 7 and SEQ ID NO.: 8 (Ct value=20.06), and further the effective PCR result was calculated in the third reaction chamber (3) (Ct value=22.55). Such PCR results can be confirmed again by the electrophoresis photograph of FIG. 33. On the other hand, according to FIG. 34, as the result graphs of real-time PCR produced by the PCR device of other company, it was confirmed again that the negative control (NC) of the first reaction chamber (1) had no reaction (Ct value=0), the effective PCR result was calculated in the second reaction chamber (2) due to the primer sets of SEQ ID NO.: 7 and SEQ ID NO.: 8 (Ct value=21.48), and further the effective PCR result was calculated in the third reaction chamber (3) (Ct value=23.83). Such PCR results can be confirmed again by electrophoresis photograph of FIG. 35.

Regarding the results of the experiments, the time relating to one example of the present invention was three times shorter than that of the apparatus belonging to another company. The time it took to reach the goal total of 40 PCR cycles was approximately 22 minutes in the case of the PCR apparatus according to one example of the present invention and about 63 minutes in the case of the PCR apparatus of another company. Further, according to FIGS. 20 to 35, it was identified that all PCR results for four kinds of food-borne bacteria from the PCR apparatus of one example of the present invention and the PCR apparatus of other company were effective.

The invention claimed is:

1. A micro Polymerase Chain Reaction (PCR) chip, comprising: a reaction chamber having an opened upper surface intended to receive a fluid; and a cover intended to seal the reaction chamber, the cover comprising a light-transmitting portion of a light transmitting material which is faced with the opened upper surface of the PCR reaction chamber to close the open upper surface, the light-transmitting portion having a protruding part that extends toward the interior of the reaction chamber from regions of closed surfaces faced on the opened upper surface of the chamber, and the end of the protruding part being adjacent to or in contact with the surface of said fluid, wherein the protruding part of the light-transmitting portion is located in an optical path between a light-emitting module and a light-detecting module for detecting optical signals in said fluid.

2. The micro PCR chip according to claim 1, wherein the reaction chamber comprises one or more PCR primer sets for detecting food-borne bacteria.

3. The micro PCR chip according to claim 2, wherein the one or more PCR primer sets are selected from the group consisting of:
a primer set for detecting *Salmonella* spp. gene, which consists of a primer comprising 15 or more consecutive nucleotides of the base sequence of SEQ ID NO: 1 and a primer comprising 15 or more consecutive nucleotides of the base sequence of SEQ ID NO: 2;
a primer set for detecting *Listeria monocytogenes* gene consists of a primer comprising 15 or more consecutive nucleotides of the base sequence of SEQ ID NO: 3 and a primer comprising 15 or more consecutive nucleotides of the base sequence of SEQ ID NO: 4;
a primer set for detecting *Staphylococcus aurens* gene which consists of a primer comprising 15 or more consecutive nucleotides of the base sequence of SEQ ID NO: 5 and a primer comprising 15 or more consecutive nucleotides of the base sequence of SEQ ID NO: 6; and
a primer set for detecting *Escherichia coli* gene which consists of a primer comprising 15 or more consecutive nucleotides of the base sequence of SEQ ID NO: 7 and a primer comprising 15 or more consecutive nucleotides of the base sequence of SEQ ID NO: 8.

4. A method for detecting *Salmonella* spp., comprising applying the micro PCR chip of claim 2 in a real-time PCR assay using the primer set consisting of a primer comprising 15 or more consecutive nucleotides of the base sequence of HQ ID NO: 1 and a primer comprising 15 or more consecutive nucleotides of the base sequence of SEQ ID NO: 2, thereby detecting said bacteria.

5. A method for detecting *Listeria monocytogenes*, comprising applying the micro PCR chip of claim 2 in a real-time PCR assay using the primer set consisting of a primer comprising 15 or more consecutive nucleotides of the base sequence of SEQ ID NO: 3 and a primer comprising 15 or more consecutive nucleotides of the base sequence of SEQ ID NO: 4, thereby detecting said bacteria.

6. A method for detecting *Staphylococcus aurens*, comprising applying the micro PCR chip of claim 2 in a real-time PCR assay using the primer set consisting of a primer comprising 15 or more consecutive nucleotides of the base sequence of SEQ ID NO: 5 and a primer comprising 15 or more consecutive nucleotides of the base sequence of SEQ ID NO: 6, thereby detecting said bacteria.

7. A method for detecting *Escherichia coli*, comprising applying the micro PCR chip of claim 2 in a real-time PCR assay using the primer set consisting of a primer comprising 15 or more consecutive nucleotides of the base sequence of SEQ ID NO: 7 and a primer comprising 15 or more consecutive nucleotides of the base sequence of SEQ. ID NO: 8, thereby detecting said bacteria.

8. The micro PCR chip according to claim 1, wherein said fluid received in the reaction chamber has a volume of 10 μl or less.

9. The micro PCR chip according to claim 8, wherein said fluid received in the reaction chamber has a volume ranging from around 5 μl to around 8 μl.

10. The micro PCR chip according to claim 1, wherein the light-transmitting portion is positioned at the center of the cover and the protruding part of the light-transmitting portion is positioned at the interior center of the reaction chamber.

11. The micro PCR chip according to claim 10, wherein the cover and the opening of the reaction chamber have a circular shape and the light-transmitting portion has a cylindrical shape.

12. A real-time PCR plate, comprising a plurality of the micro PCR chips according to claim 1.

13. The real-time PCR plate according to claim 12, comprising:
 a first plate in a flat-plate shape, being a support for said real-time PCR plate;
 a second plate in a flat-plate shape, comprising the reaction chambers of the micro PCR chips and disposed on the first plate; and
 a third plate in a flat-plate shape, comprising the covers of the micro PCR chips, the covers configured to respectively seal the corresponding reaction chambers when the third plate is disposed on the second plate.

14. The real-time PCR plate according to claim 13, further comprising a heat-releasing module configured to release the heat from the reaction chambers.

15. The real-time PCR plate according to claim 14, wherein the reaction chambers comprise one or more PCR primer sets for detecting food-borne bacteria.

16. A real-time PCR apparatus, comprising:
 the real-time PCR plate according to claim 14;
 a first heat block configured to heat the real-time PCR plate when in contact therewith;
 a second heat block positioned a distance away from the first heat block and configured to heat the real-time PCR plate when in contact therewith;
 a light-emitting module;
 a light-detecting module; and
 a plate-moving means configured to move the real-time PCR plate between the first heat block and the second heat block,
 wherein the light-emitting module and the light-detecting module are configure to optically detect an on-going PCR reaction in the reaction chambers when the real-time PCR plate moves between the first heat block and the second heat block by the plate-moving means.

17. The real-time PCR apparatus according to claim 16, wherein the first heat block has a temperature of 90° C. to 100° C. and the second heat block has a temperature of 55° C. to 75° C.

18. The real-time PCR apparatus according to claim 17, wherein the first heat block has a temperature of around 95° C. and the second heat block has a temperature of about 72° C.

19. The real-time PCR apparatus according to claim 17, wherein the reaction chambers comprise one or more PCR primer sets for detecting food-borne bacteria.

* * * * *

```
                        SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: synthesized

<400> SEQUENCE: 1
tgttgcggaa cgcgcttgat gagcttt                                        27

<210> SEQ ID NO 2
<211> LENGTH: 28
<212> TYPE: DNA
<213> ORGANISM: Artificial Sequence
<220> FEATURE:
<223> OTHER INFORMATION: synthesized

<400> SEQUENCE: 2
caggaaattt cgcttccagt tggtccag                                       28

<210> SEQ ID NO 3
<211> LENGTH: 25
<212> TYPE: DNA
<213> ORGANISM: Artificial Sequence
<220> FEATURE:
<223> OTHER INFORMATION: synthesized

<400> SEQUENCE: 3
gcgccactac ggacgtttaa ccaag                                          25

<210> SEQ ID NO 4
<211> LENGTH: 25
<212> TYPE: DNA
<213> ORGANISM: Artificial Sequence
<220> FEATURE:
<223> OTHER INFORMATION: synthesized

<400> SEQUENCE: 4
acaatcgcat ccgcaagcac tgtag                                          25

<210> SEQ ID NO 5
<211> LENGTH: 30
<212> TYPE: DNA
<213> ORGANISM: Artificial Sequence
<220> FEATURE:
<223> OTHER INFORMATION: synthesized

<400> SEQUENCE: 5
attggttgat acacctgaaa caaagcatcc                                     30
```

```
<210> SEQ ID NO 6
<211> LENGTH: 30
<212> TYPE: DNA
<213> ORGANISM: Artificial Sequence
<220> FEATURE:
<223> OTHER INFORMATION: synthesized

<400> SEQUENCE: 6
aaagcttcgt ttaccatttt tccatcagca                                    30

<210> SEQ ID NO 7
<211> LENGTH: 24
<212> TYPE: DNA
<213> ORGANISM: Artificial Sequence
<220> FEATURE:
<223> OTHER INFORMATION: synthesized

<400> SEQUENCE: 7
atgtggccgg gttcgttaat acgg                                          24

<210> SEQ ID NO 8
<211> LENGTH: 24
<212> TYPE: DNA
<213> ORGANISM: Artificial Sequence
<220> FEATURE:
<223> OTHER INFORMATION: synthesized

<400> SEQUENCE: 8
gctgcgacac gttgcagagt ggta                                          24
```